US008765407B2

(12) United States Patent
Iyo et al.

(10) Patent No.: US 8,765,407 B2
(45) Date of Patent: Jul. 1, 2014

(54) L-AMINO ACID PRODUCING BACTERIUM AND METHOD OF PRODUCING L-AMINO ACID

(75) Inventors: Mayu Iyo, Kawasaki (JP); Ryo Takeshita, Kawasaki (JP); Shinichi Sugimoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 375 days.

(21) Appl. No.: 12/179,988

(22) Filed: Jul. 25, 2008

(65) Prior Publication Data

US 2009/0215130 A1 Aug. 27, 2009

Related U.S. Application Data

(63) Continuation of application No. PCT/JP2007/051878, filed on Jan. 30, 2007.

(30) Foreign Application Priority Data

Jan. 30, 2006 (JP) .................................. 2006-020563
Sep. 7, 2006 (JP) .................................. 2006-243282

(51) Int. Cl.
*C12P 21/04* (2006.01)
*C12P 21/06* (2006.01)

(52) U.S. Cl.
USPC ......................... 435/69.1; 435/71.1; 435/71.2

(58) Field of Classification Search
None
See application file for complete search history.

(56) References Cited

U.S. PATENT DOCUMENTS

| | | | |
|---|---|---|---|
| 3,293,141 A * | 12/1966 | Mateles et al. ............... | 435/108 |
| 3,616,224 A * | 10/1971 | Shiio et al. ................... | 435/106 |
| 4,347,318 A * | 8/1982 | Miwa et al. ................... | 435/115 |
| 5,661,012 A | 8/1997 | Sano et al. | |
| 5,827,698 A | 10/1998 | Kikuchi et al. | |
| 5,830,716 A | 11/1998 | Kojima et al. | |
| 5,932,453 A | 8/1999 | Kikuchi et al. | |
| 6,040,160 A | 3/2000 | Kojima et al. | |
| 6,878,533 B2 | 4/2005 | Tsujimoto et al. | |
| 6,905,819 B1 | 6/2005 | Matsuzaki et al. | |
| 6,911,332 B2 | 6/2005 | Usuda et al. | |
| 7,026,149 B2 | 4/2006 | Usuda et al. | |
| 7,029,893 B2 | 4/2006 | Usuda et al. | |
| 7,060,475 B2 | 6/2006 | Usuda et al. | |
| 7,160,704 B2 | 1/2007 | Takeshita et al. | |
| 7,192,747 B2 | 3/2007 | Ono et al. | |
| 7,192,748 B2 | 3/2007 | Usuda et al. | |
| 7,211,421 B2 | 5/2007 | Tsujimoto et al. | |
| 7,220,570 B2 | 5/2007 | Usuda et al. | |
| 7,223,572 B1 | 5/2007 | Gunji et al. | |
| 7,244,569 B2 | 7/2007 | Matsuzaki et al. | |
| 7,306,933 B2 | 12/2007 | Dien et al. | |
| 2002/0025564 A1 | 2/2002 | Kobayashi et al. | |
| 2002/0155556 A1 | 10/2002 | Imaizumi et al. | |
| 2002/0160461 A1 | 10/2002 | Nakai et al. | |
| 2004/0229305 A1 | 11/2004 | Usuda et al. | |
| 2005/0176121 A1 | 8/2005 | Takeshita et al. | |
| 2005/0214911 A1 | 9/2005 | Marchenko et al. | |
| 2006/0019355 A1 | 1/2006 | Ueda et al. | |
| 2006/0019356 A1 | 1/2006 | Usuda et al. | |
| 2006/0030010 A1 | 2/2006 | Usuda et al. | |
| 2006/0030011 A1 | 2/2006 | Usuda et al. | |
| 2007/0243590 A1 | 10/2007 | Takeshita et al. | |
| 2007/0249017 A1 | 10/2007 | Usuda et al. | |

FOREIGN PATENT DOCUMENTS

| | | |
|---|---|---|
| EP | 1 577 396 | 9/2005 |
| WO | WO01/53459 | 7/2001 |
| WO | WO02/29034 | 4/2002 |
| WO | WO2005/064001 | 7/2005 |
| WO | WO2006/038695 | 4/2006 |
| WO | WO2007/069782 | 6/2007 |

OTHER PUBLICATIONS

Postle et al., 1983, PNAS, USA, 80: 5235-5239.*
Buchanan, S. K., et al., "Crystal structure of the outer membrane active transporter FepA from *Escherichia coli*," Nature Structural Biol. 1999;6(1):56-63.
Chakraborty, R., et al., "Identification and mutational studies of conserved amino acids in the outer membrane receptor protein, FepA, which affect transport but not binding of ferric-enterobactin in *Escherichia coli*," BioMetals 2003;16(4):507-518.
Ferguson, A. D., et al., "Structural Basis of Gating by the Outer Membrane Transporter FecA," Science 2002;295(5560):1715-1719.
Howard, S. P., et al., "In Vivo Synthesis of the Periplasmic Domain of TonB Inhibits Transport through the FecA and FhuA Iron Siderophore Transporters of *Escherichia coli*," J. Bacteriol. 2001;183(20):5885-5895.
Killmann, H., et al., "TonB of *Escherichia coli* activates FhuA through interaction with the β-barrel," Microbial. 2002;148(11):3497-3509.
Ogierman, M., et al., "Interactions between the Outer Membrane Ferric Citrate Transporter FecA and TonB: Studies of the FecA TonB Box," J. Bacteriol. 2003;185(6):1870-1885.
International Search Report and Written Opinion of the International Searching Authority for PCT Patent App. No. PCT/JP2007/051878 (Apr. 19, 2007).
Garcia-Herrero, A., et al., "Nuclear magnetic resonance solution structure of the periplastic signalling domain of the TonB-dependent oufer membrane transporter FecA from *Escherichia coli*," Mol. Microbiol. 2005;58(5):1226-1237.

(Continued)

*Primary Examiner* — Albert Navarro
(74) *Attorney, Agent, or Firm* — Shelly Guest Cermak; Cermak Nakajima LLP

(57) ABSTRACT

An L-amino acid is produced by culturing an L-amino acid-producing bacterium which belongs to the Enterobacteriaceae family and which has been modified so that the activity of an iron transporter is increased by enhancing expression of one or more genes of the following genes: tonB gene, fepA gene, and fecA.

6 Claims, No Drawings

(56) References Cited

OTHER PUBLICATIONS

Howard, S. P., et al., "In Vivo Synthesis of the Periplastic Domain of TonB Inhibits Transport through the FecA and FhuA Iron Siderophore Transporters of *Escherichia coli*," J. Bacteriol. 2001;183(20):5885-5895.

Murphy, C. K., et al., "Surface Topology of the *Escherichia coli* K-12 Ferric Enterobactin Receptor," J. Bacteriol. 1990;172(5):2736-2746.
Ogierman, M., et al., "Interactions between the Outer Membrane Ferric Citrate Transporter FecA and TonB: Studies of the FecA TonB Box," J. Bacteriol. 2003;185(6):1870-1885.
International Preliminary Report on Patentability for PCT Patent App. No. PCT/JP2007/051878 (Aug. 14, 2008).

* cited by examiner

US 8,765,407 B2

L-AMINO ACID PRODUCING BACTERIUM AND METHOD OF PRODUCING L-AMINO ACID

This application is a continuation under 35 U.S.C. §120 of PCT/JP2007/051878, filed Jan. 30, 2007, and claims priority under 35 U.S.C. §119 to Japanese Patent Application No. 2006-020563, filed on Jan. 30, 2006, and Japanese Patent Application No. 2006-243282, filed Sep. 7, 2006, all of which are incorporated by reference. The Sequence Listing filed electronically herewith is also hereby incorporated by reference in its entirety (File Name: US-321_Seq_List_Copy_1; File Size: 72 KB; Date Created: Jul. 25, 2008).

BACKGROUND OF THE INVENTION

1. Field of the Invention

The present invention relates to a method of producing an L-amino acid using a bacterium, and more particularly, to a method of producing an L-amino acid such as L-lysine, L-threonine, and L-glutamic acid. L-lysine and L-threonine are useful as additives in animal feeds, components of health food, amino acid infusions, and the like. L-glutamic acid is useful as a food seasoning.

2. Brief Description of the Related Art

L-amino acids have been industrially produced by fermentation using bacteria belonging to the genus *Brevibacterium, Corynebacterium, Escherichia*, or the like. Methods of producing L-lysine are described in EP 0643135 B, EP 0733712 B, EP 1477565 A, EP 0796912 A, EP 0837134 A, WO 01/53459, EP 1170376 A, and WO 2005/010175. In these methods, bacterial strains are used which are isolated from nature or artificial mutants thereof, as well as bacterial strains which have been modified to enhance the activity of an L-amino acid biosynthetic enzyme by recombinant DNA techniques.

Methods are known for improving L-amino acid-producing ability, and include modifying the uptake or export of L-amino acids in and out of cells. A known method of enhancing L-amino acid export is to produce L-lysine (WO 97/23597) or L-arginine (US 2003-0113899) using a bacterial strain belonging to the genus *Corynebacterium* which has been modified so that expression of an L-lysine/L-arginine export gene (LysE) is enhanced. In addition, methods have been reported of producing an L-amino acid using a bacterium belonging to the Enterobacteriaceae family which has been modified so that expression is enhanced of the rhtA gene, rhtB gene, and rhtC gene (EP 1013765 A), yfiK gene or yahN gene (EP 1016710 A), ybjE gene (WO 2005/073390), or yhfk gene (WO 2005/085419). Each of these genes have been suggested to be involved in L-amino acid export.

It is also known that enhancing the expression of an uptake gene for a sugar improves the L-amino acid-producing ability. This is because sugars typically function as a substrate during fermentation. Examples of such methods include producing an L-amino acid using an *Escherichia* bacterium modified to have enhanced expression of the ptsG gene (WO 03/04670), ptsH gene, ptsI gene, or crr gene (WO 03/04674).

The fepA gene and the fecA gene each encode a membrane protein which is known as an iron transporter, while the tonB gene encodes a protein that regulates the activity of the iron transporter (J. Bacteriol. 1990; 172(5): 2736-46, J. Bacteriol, 2003, vol. 185, No. 6, p 1870-1885, Mol. Microbiol. 2005; 58(5): 1226-1237, J. Bacteriol 2001, vol. 183, No. 20, p 5885-5895). However, there have been no reports that enhancing the activities of these gene products can be effective for L-amino acid production.

SUMMARY OF THE INVENTION

An object of the present invention is to provide a bacterium which is capable of effectively producing an L-amino acid and a method of effectively producing an L-amino acid using the bacterium.

The inventors of the present invention have made extensive studies to solve the above-mentioned object. As a result, they have found that production of an L-amino acid is improved by amplifying each of the genes encoding proteins involved in the tonB system in an L-amino acid producing bacterium, and thus have completed the present invention. That is, the present invention is as follows.

It is an object of the present invention to provide a L-amino acid-producing bacterium belonging to the Enterobacteriaceae family which has been modified to enhance the expression of the gene encoding a protein of the tonB system, and wherein said gene is selected from the group consisting of the tonB gene, fepA gene, fecA gene, and combinations thereof.

It is another object of the present invention to provide the bacterium as described above, wherein the expression is enhanced by increasing the copy number of said gene(s) or by modifying an expression regulatory sequence of said gene.

It is another object of the present invention to provide the bacterium as described above, wherein said tonB gene encodes a protein having the amino acid sequence of SEQ ID NO: 2 or a protein having an amino acid sequence of SEQ ID NO: 2, wherein said sequence includes substitutions, deletions, insertions, or additions of one or several amino acids and wherein said protein regulates the activity of the iron transporter.

It is another object of the present invention to provide the bacterium as described above, wherein said fepA gene encodes a protein having the amino acid sequence of SEQ ID NO: 4 or a protein having an amino acid sequence of SEQ ID NO: 4, wherein said sequence includes substitutions, deletions, insertions, or additions of one or several amino acids, and wherein said protein has iron transporter activity.

It is another object of the present invention to provide the bacterium as described above, wherein said fecA gene encodes a protein having the amino acid sequence of SEQ ID NO: 10 or a protein having an amino acid sequence of SEQ ID NO: 10, wherein said sequence includes substitutions, deletions, insertions, or additions of one or several amino acids, wherein said protein has iron transporter activity.

It is another object of the present invention to provide the bacterium as described above, wherein said tonB gene is selected from the group consisting of:
  (a) a DNA comprising the nucleotide sequence of SEQ ID NO: 1; and
  (b) a DNA that hybridizes with a nucleotide sequence which is complementary to the nucleotide sequence of SEQ ID NO: 1 or with a probe that is prepared from the nucleotide sequence under stringent conditions, and wherein said DNA encodes a protein that is able to regulate the activity of the iron transporter.

It is another object of the present invention to provide the bacterium as described above, wherein said fepA gene is selected from the group consisting of:
  (c) a DNA comprising the nucleotide sequence of SEQ ID NO: 3; and
  (d) a DNA that hybridizes with a nucleotide sequence which is complementary to the nucleotide sequence of SEQ ID NO: 3 or a probe that is prepared from the nucleotide sequence under stringent conditions, and wherein said DNA encodes a protein that has iron transporter activity.

It is another object of the present invention to provide the bacterium as described above, wherein the fecA gene is selected from the group consisting of:
(e) a DNA comprising the nucleotide sequence of SEQ ID NO: 9; and
(f) a DNA that hybridizes with a nucleotide sequence which is complementary to the nucleotide sequence of SEQ ID NO: 9 or a probe that is prepared from the nucleotide sequence under stringent conditions, and wherein said DNA encodes a protein that has iron transporter activity.

It is another object of the present invention to provide the bacterium as described above, wherein the L-amino acid is selected from the group consisting of L-lysine, L-arginine, L-histidine, L-isoleucine, L-valine, L-leucine, L-threonine, L-phenylalanine, L-tyrosine, L-tryptophan, L-cysteine, L-glutamic acid, and combinations thereof.

It is another object of the present invention to provide the bacterium as described above, wherein said bacterium belongs to the genus *Escherichia, Pantoea,* or *Enterobacter.*

It is another object of the present invention to provide a method of producing an L-amino acid, comprising culturing the bacterium as described above in a medium to produce and accumulate an L-amino acid in the medium or bacterial cells, and collecting the L-amino acid from the medium or bacterial cells.

It is another object of the present invention to provide the method as described above, wherein said L-amino acid is selected from the group consisting of L-lysine, L-arginine, L-histidine, L-isoleucine, L-valine, L-leucine, L-threonine, L-phenylalanine, L-tyrosine, L-tryptophan, L-cysteine, L-glutamic acid, and combinations thereof.

DESCRIPTION OF THE PREFERRED EMBODIMENTS

Hereinafter, the present invention will be described in detail.

<1> Bacterium of the Present Invention

The bacterium of the present invention belongs to the Enterobacteriaceae family, and has an L-amino acid-producing ability, and is modified so that the activity of an iron transporter is enhanced by enhancing the expression of a gene encoding a protein of the tonB system. Herein, the term "L-amino acid-producing ability" refers to the ability to produce and accumulate an L-amino acid in a medium at a collectable level when the bacterium of the present invention is cultured in the medium. The bacterium of the present invention may be able to produce a plurality of L-amino acids. The L-amino acid-producing ability may be native to the bacterium, or may be obtained by modifying the bacterium to impart the L-amino acid-producing ability by mutation or a recombinant DNA technique.

The kind of L-amino acid is not particularly limited, and examples thereof include the basic L-amino acids such as L-lysine, L-ornithine, L-arginine, L-histidine and L-citrulline; the aliphatic L-amino acids such as L-isoleucine, L-alanine, L-valine, L-leucine, and L-glycine; the hydroxy monoaminocarboxylic acids such as L-threonine and L-serine; the cyclic L-amino acids such as L-proline; the aromatic L-amino acids such as L-phenylalanine, L-tyrosine, and L-tryptophan; the sulfur-containing L-amino acids such as L-cysteine, L-cystine, and L-methionine; and the acidic L-amino acids such as L-glutamic acid, L-aspartic acid, L-glutamine, and L-asparagine. The bacterium of the present invention may be able to produce two or more kinds of amino acids.

<1-1> Imparting L-Amino Acid-Producing Ability

Hereinafter, methods of imparting the L-amino acid-producing ability will be described, as well as examples of the bacteria to which an L-amino acid-producing ability can be imparted. However, the bacterium is not limited thereto, as long as it has an L-amino acid-producing ability.

Bacteria belonging to the Enterobacteriaceae family, including those belonging to the genus *Escherichia* or *Pantoea*, can be used as the parent strain from which to derive the bacterium of the present invention. Other examples of bacteria belonging to the Enterobacteriaceae family include γ-Proteobacteria such as *Enterobacter, Klebsiella, Serratia, Erwinia, Salmonella,* and *Morganella. Escherichia* bacteria reported in Neidhardt et al. ((Backmann, B. J. 1996. Derivations and Genotypes of some mutant derivatives of *Escherichia coli* K-12, p. 2460-2488. Table 1. In F. D. Neidhardt (ed.), *Escherichia coli* and *Salmonella* Cellular and Molecular Biology/Second Edition, American Society for Microbiology Press, Washington, D.C.), such as *Escherichia coli* can be utilized. Examples of a wild-type strain of *Escherichia coli* include the K-12 strain or derivatives thereof, *Escherichia coli* MG1655 strain (ATCC No. 47076), and W3110 strain (ATCC No. 27325). These strains are available from the American Type Culture Collection (ATCC) (Address: P.O. Box 1549, Manassas, Va. 20108, 1, United States of America).

Examples of *Enterobacter* bacteria include *Enterobacter agglomerans* and *Enterobacter aerogenes*, and an example of *Pantoea* bacteria is *Pantoea ananatis*. Recently, *Enterobacter agglomerans* was reclassified in some cases as *Pantoea agglomerans, Pantoea ananatis, Pantoea stewartii*, or the like, based on an analysis of the nucleotide sequence of 16S rRNA. Therefore, bacteria of the present invention may belong to either the genus *Enterobacter* or the genus *Pantoea*, as long as they are classified in the Enterobacteriaceae family. When *Pantoea ananatis* is bred using genetic engineering techniques, *Pantoea ananatis* AJ13355 strain (FERM BP-6614), AJ13356 strain (FERM BP-6615), AJ13601 strain (FERM BP-7207), derivatives thereof, and the like, may be used. These strains were identified and deposited as *Enterobacter agglomerans* when they were isolated, but as described above, these strains have been reclassified as *Pantoea ananatis* based on an analysis of the nucleotide sequence of 16S rRNA.

The L-amino acid-producing ability can be imparted to a parent strain as described above, as follows.

In order to impart the L-amino acid-producing ability, methods may be used which are used in conventional breeding of *Escherichia* bacteria or the like, such as by acquiring nutrient-auxotrophic mutant strains, analogue resistant strains, or metabolic regulation mutant strains, or by creating recombinant strains having enhanced expression of L-amino acid biosynthetic enzymes (Amino Acid Fermentation, Japan Scientific Societies Press, first edition publication: May 30, 1986, p. 77 to 100). In the present invention, properties such as nutrient-auxotrophy, analogue-resistance, and metabolic regulation may be imparted alone or in combination with imparting the L-amino acid-producing ability. Furthermore, expression of one or more L-amino acid biosynthetic enzymes may be enhanced. Furthermore, imparting of such properties as nutrient-auxotrophy, analogue-resistance and metabolic regulation mutation may be combined with enhancing the expression of the L-amino acid biosynthetic enzymes.

Nutrient-auxotrophic mutant strains, L-amino acid-analogue resistant strains, and metabolic regulation mutant strains that have an L-amino acid-producing ability can be obtained as follows. A parent strain or a wild-type strain is subjected to a typical mutation treatment, such as irradiation with X-rays or ultraviolet rays, or by treating with a mutagen, including N-methyl-N'-nitro-N-nitrosoguanidine (NTG) and ethylmethanesulfonate (EMS), followed by selection of the strains that exhibit nutrient-auxotrophy, analogue-resistance, or a metabolic regulation mutation and have an L-amino acid-producing ability.

Examples of an L-lysine analogue include oxalysine, lysine hydroxamate, S-(2-aminoethyl)-L-cysteine (AEC), γ-methyllysine, α-chlorocaprolactam, and norleucine. Examples of an L-arginine analogue include arginine hydroxamate, homoarginine, D-arginine, and canavanine.

Specific examples of an L-lysine analogue resistant strain or metabolic regulation mutant strain having an L-lysine-producing ability include *Escherichia coli* AJ11442 (FERM BP-1543, NRRL B-12185; JP 56-18596 A and U.S. Pat. No. 4,346,170) and *Escherichia coli* VL611 (JP 2000-189180 A). The WC196 strain (WO 96/17930) may be used as an L-lysine producing strain of *Escherichia coli*. The WC1-96 strain was obtained by imparting AEC (S-(2-aminoethyl)-cysteine)-resistance to the W3110 strain, which was derived from *Escherichia coli* K-12 strain. The WC196 strain was named *Escherichia coli* AJ13069 and deposited at the National Institute of Bioscience and Human-Technology, Agency of Industrial Science and Technology (currently, International Patent Organism Depositary, National Institute of Advanced Industrial Science and Technology, Central 6, 1-1-1 Higashi, Tsukuba, Ibaraki 305-8566, Japan) on Dec. 6, 1994 and given an accession number of FERM P-14690, and the deposit was then converted to an international deposit under the provisions of Budapest Treaty on Sep. 29, 1995 and given an accession number of FERM BP-5252.

An L-amino acid-producing ability can also be imparted by enhancing the expression of a gene encoding an L-amino acid biosynthetic enzyme.

For example, as described below, an L-lysine-producing ability may be imparted by enhancing the activities of dihydrodipicolinate synthase and aspartokinase. That is, a gene fragment encoding dihydrodipicolinate synthase and a gene fragment encoding aspartokinase are ligated to a vector which functions in the host bacterium. The vector is preferably a multi-copy vector, and is used to transform the host bacterium. The transformation results in increased copy numbers of the gene encoding dihydrodipicolinate synthase and the gene encoding aspartokinase in the host cell, thereby enhancing the activities of these enzymes. Hereinafter, dihydrodipicolinate synthase, aspartokinase, and aspartokinase III are abbreviated as DDPS, AK, and AKIII, respectively.

The genes encoding DDPS and AK are not particularly limited as long as the DDPS and AK activities are expressed in the host bacterium, and examples thereof include the genes of *Escherichia coli*, *Methylophilus methylotrophus*, *Corynebacterium glutamicum*, and the like. The nucleotide sequences of the DDPS gene derived from an *Escherichia* bacterium (dapA, Richaud, F. et al. J. Bacteriol., 297 (1986)) and the AKIII gene derived from an *Escherichia* bacterium (lysC, Cassan, M., Parsot, C., Cohen, G. N. and Patte, J. C., J. Biol. Chem., 261, 1052 (1986)) have been identified, so these genes can be obtained by PCR using primers synthesized based on their nucleotide sequences and the chromosomal DNA of *Escherichia coli* K-12, for example, as a template.

Hereinafter, dapA and lysC derived from *Escherichia coli* will be exemplary, but the genes encoding DDPS and AK are not limited thereto.

It is known that the wild-type DDPS derived from *Escherichia coli* is regulated by feedback inhibition by L-lysine, while the wild-type AKIII derived from *Escherichia coli* is regulated by suppression and feedback inhibition by L-lysine. Therefore, when using dapA and lysC, mutated forms of these genes are preferable so that the genes are not subject to feedback inhibition. However, the DDPS and AK of the present invention are not necessarily these mutants since the DDPS derived from *Corynebacterium* bacterium is not subject to feedback inhibition.

An example of a DNA encoding mutant DDPS which is not subject to feedback inhibition by L-lysine includes a DNA encoding DDPS which has an amino acid sequence in which the histidine at position 118 is substituted with tyrosine. Meanwhile, an example of a DNA encoding mutant AKIII which is not subject to feedback inhibition by L-lysine includes a DNA encoding an AKIII having an amino acid sequence in which the threonine at position 352, the glycine at position 323, and the methionine at position 318 are replaced with isoleucine, asparagine and isoleucine, respectively (U.S. Pat. No. 5,661,012 and U.S. Pat. No. 6,040,160). Such mutant DNAs can be obtained by site-specific mutation using PCR or the like.

Enhancing expression of the L-lysine biosynthetic genes as described above can be attained by transformation or homologous recombination using a plasmid or the like, in the same way as the tonB gene, fepA gene, and fecA gene described below.

Wide host-range plasmids RSFD80, pCAB1, and pCABD2 contain a mutant dapA gene encoding a mutant DDPS and a mutant lysC gene encoding a mutant AKIII (U.S. Pat. No. 6,040,160). *Escherichia coli* JM109 strain transformed with RSFD80 was named AJ12396 (U.S. Pat. No. 6,040,160), and the strain was deposited at the National Institute of Bioscience and Human-Technology, Agency of Industrial Science and Technology, Ministry of International Trade and Industry (currently, International Patent Organism Depositary, National Institute of Advanced Industrial Science and Technology) on Oct. 28, 1993 and given an accession number of FERM P-13936, and the deposit was then converted to an international deposit under the provisions of Budapest Treaty on Nov. 1, 1994 and given an accession number of FERM BP-4859. RSFD80 can be obtained from AJ12396 strain by a conventional method.

An L-lysine-producing ability can also be imparted by enhancing expression of genes encoding enzymes, other than DDPS and AK, which are involved in biosynthesis of L-lysine. Examples of such enzymes include proteins of the diaminopimelate pathway such as dihydrodipicolinate reductase (dapB: hereinafter, the words in parentheses are the gene names) (WO01/53459), diaminopimelate decarboxylase (lysA), diaminopimelate dehydrogenase (ddh) (WO96/40934), phosphoenolpyruvate carboxylase (pepC) (JP 60-87788 A), aspartate aminotransferase (aspC) (JP 06-102028 B), diaminopimelate epimerase gene (dapF) (JP 2003-135066), aspartate semialdehyde dehydrogenase (asd) (WO 00/61723), tetrahydrodipicolinate succinylase (dapD), and succinyl-diaminopimelate deacylase (dapE). Further examples are proteins of the aminoadipic acid pathway such as homoaconitate hydratase (JP 2000-157276 A). The documents indicated in parentheses disclose L-lysine-producing strains having enhanced expression of a gene encoding each enzyme. Enhancing expression of a gene encoding each enzyme may be combined with enhancing expression of the DDPS and AK genes.

Expression of genes other than L-lysine biosynthetic genes may also be enhanced, and such genes include those encoding enzymes involved in sugar uptake, sugar metabolism (glycolytic pathway), the TCA cycle, the pentose phosphate cycle, complementary pathway, and energy metabolism. Moreover, the expression may also be enhanced of genes that impart amino acid-resistance to a host bacterium, genes encoding amino acid-export enzymes, and genes encoding enzymes involved in uptake of by-products. Enhancing the expression of these genes is useful for the production of all kinds of L-amino acids.

Genes involved in sugar metabolism include genes encoding enzymes in the glycolytic pathway or enzymes involved in sugar uptake. Examples thereof include the glucose-6-phosphate isomerase gene (pgi; WO 01/02542), phosphoenolpyruvate synthase gene (pps; EP 877090 A), phosphoglucomutase gene (pgm; WO 03/04598), fructose bisphosphate aldolase gene (fbp; WO 03/04664), pyruvate kinase gene (pykF; WO 03/008609), transaldolase gene (talB; WO 03/008611), fumarase gene (fum; WO 01/02545), phosphoenolpyruvate synthase gene (pps; EP 877090 A), non-PTS sucrose uptake gene (csc; EP 149911 A), sucrose-assimilating gene (scrAB operon; WO 90/04636), PTS glucose uptake gene (ptsG, ptsH, ptsI, crr; WO 03/04670, WO 03/04674, and EP 1254957 A), galactose-proton symporter gene (galP; US2004-214294), D-xylose permease gene (xylE; WO2006/043730□ and a gene involved in maltose transport (malK; EP 1254957).

Examples of genes encoding the TCA cycle enzymes include the citrate synthase gene (gltA; WO 03/008607), isocitrate dehydrogenase gene (icd; WO 03/008607), 2-ketoglutarate dehydrogenase gene (sucAB; WO 03/008614), succinate dehydrogenase gene (sdh; WO 01/02544), and glutamate dehydrogenase gene (gdh; WO00/53726).

Examples of genes encoding the pentose phosphate cycle enzymes include the glucose-6-phosphate dehydrogenase gene (zwf; WO 03/008607) and ribose-5-phosphate isomerase gene (rpiB; WO 03/008607).

Examples of genes encoding the anaplerotic pathway include the phosphoenolpyruvate carboxylase gene (pepC; U.S. Pat. No. 5,876,983), pyruvate carboxylase gene (pyc; EP 1092776), malate dehydrogenase gene (mdh; WO 01/02546), and phosphoenolpyruvate carboxykinase gene (pckA; WO 04/090125).

Examples of genes encoding enzymes involved in energy metabolism include the transhydrogenase gene (pntAB; U.S. Pat. No. 5,830,716) and cytochromoe bo type oxidase gene (cyoB; EP 1070376).

Examples of genes that impart L-amino acid-resistance include the rhtB gene (U.S. Pat. No. 6,887,691), rhtC gene (EP 1013765), yedA gene (EP 1449917), yddG gene (EP 1449918), ygaZH gene (EP 1239041), yahN, yfiK, and yeaS genes (EP 1016710), rhtA gene (Res Microbiol. 2003 March; 154(2): 123-35), and ybjE gene (WO 2005/073390).

Furthermore, in the bacterium of the present invention, the activity of an enzyme that catalyzes a reaction which branches off from the L-lysine biosynthetic pathway and produces a compound other than L-lysine may be decreased or may be made deficient. Examples of such an enzyme include homoserine dehydrogenase, lysine decarboxylase, and malic enzyme, and strains in which the activities of such enzymes are decreased or deficient are described in WO 95/23864, WO 96/17930, WO 2006/038695, WO 2005/010175, and the like. In *Escherichia coli*, lysine decarboxylases are encoded by the cadA gene (Genbank Accession No. NP_418555, SEQ ID NO: 17) and ldcC gene (Genbank Accession No. NP_414728, SEQ ID NO: 11) (WO 96/17930), so these genes may be disrupted to enhance L-lysine-producing ability. DNA molecules homologous to the cadA gene and ldcC gene may be used as long as they can cause homologous recombination with the cadA gene and ldcC gene on the chromosome of the host bacterium. For example, a DNA molecule homologous to the cadA gene may hybridize to the complementary strand of SEQ ID NO: 17 under stringent conditions, and a DNA molecule homologous to the ldcC gene may hybridize to the complementary strand of SEQ ID NO: 11 under stringent conditions.

Activities of these enzymes can be decreased or eliminated by introducing a mutation into the genes encoding the enzymes on the chromosome using a known mutation treatment, to thereby decrease or eliminate the activities of the enzymes in the cell. For example, decreasing or eliminating the activities of the enzymes can be attained by disrupting the genes encoding the enzymes on the chromosome by gene recombination or by modifying an expression regulatory sequence such as the promoter or Shine-Dalgarno (SD) sequence. In addition, this can also be attained by introducing an amino acid substitution (missense mutation) to the region encoding the enzymes on the chromosome, introducing a stop codon (nonsense mutation), introducing a frameshift mutation that adds or deletes one or two nucleotides, or deleting part of the gene (Journal of biological Chemistry 272: 8611-8617 (1997). Also, the activities of the enzymes can also be decreased or eliminated by constructing a mutant gene which has a deletion in the coding region, and then replacing the normal gene on the chromosome with the mutant gene by homologous recombination, or introducing the mutant gene using a transposon or an IS factor.

For example, the following gene recombination method can be used to introduce a mutation that decreases or eliminates the activities of the above-mentioned enzymes. The mutant gene is prepared by modifying a partial sequence of a target gene so that it does not encode an properly-functioning enzyme. Then, a bacterium belonging to the Enterobacteriaceae family is transformed with a DNA containing the mutant, resulting in recombination of a gene on the bacterial chromosome with the mutant gene, thereby substituting the target gene on the chromosome with the mutant gene. Examples of this type of gene substitution using homologous recombination using a linear DNA called "Red-driven integration" (Datsenko, K. A, and Wanner, B. L. Proc. Natl. Acad. Sci. USA. 97: 6640-6645 (2000), a combination of Red-driven integration and a cleavage system derived from λ phage (Cho, E. H., Gumport, R. I., Gardner, J. F. J. Bacteriol. 184: 5200-5203 (2002)) (WO 2005/010175), using a plasmid containing a temperature-sensitive replication origin (Datsenko, K. A, and Wanner, B. L. Proc. Natl. Acad. Sci. USA. 97: 6640-6645 (2000); U.S. Pat. No. 6,303,383; JP 05-007491 A), and the like. Meanwhile, site-specific mutation by gene substitution using homologous recombination can also be performed by using a plasmid which is not able to replicate in the host cell.

The above-described methods for enhancing the expression of the L-lysine biosynthetic enzymes' genes and for decreasing the activities of enzymes can also be applied to genes encoding other L-amino acid synthetic enzymes. In this way, the ability to produce another L-amino acid can be imparted to a bacterium of the Enterobacteriaceae family.

Hereinafter, a bacterium to which an ability to produce an L-amino acid other than L-lysine is imparted will be exemplified.

L-Threonine-Producing Bacteria

Examples of parent strains for deriving the L-threonine-producing bacteria of the present invention include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The TDH-6 strain is deficient in the thrc gene, as well as being sucrose-assimilative, and the ilvA gene has a leaky mutation. This strain also has a mutation in the rhtA gene, which imparts resistance to high concentrations of threonine or homoserine. The B-3996 strain contains pVIC40, which was obtained by inserting the thrA*BC operon which includes a mutant thrA gene into a RSF1010-derived vector. This mutant thrA gene encodes aspartokinase homoserine dehydrogenase I which is substantially desensitized to feedback inhibition by threonine. The B-3996 strain was deposited on Nov. 19, 1987 in the All-Union Scientific Center of Antibiotics (Nagatinskaya Street 3-A, 117105 Moscow, Russian Federation) under the accession number RIA 1867. This strain was also deposited in the Russian National Collection of Industrial Microorganisms (VKPM) (Russia, 117545 Moscow 1, Dorozhny proezd. 1) on Apr. 7, 1987 under the accession number B-3996.

*E. coli* VKPM B-5318 (EP 0593792B) may also be used to derive the L-threonine-producing bacteria of the present invention. The B-5318 strain is prototrophic with regard to isoleucine, and a temperature-sensitive lambda-phage C1 repressor and PR promoter replaces the regulatory region of the threonine operon in plasmid pVIC40. The VKPM B-5318 strain was deposited in the Russian National Collection of Industrial Microorganisms (VKPM) (Russia, 117545 Moscow 1, Dorozhny proezd. 1) on May 3, 1990 under accession number of VKPM B-5318.

Preferably, the bacterium of the present invention is additionally modified to enhance expression of one or more of the following genes:

the mutant thrA gene which codes for aspartokinase homoserine dehydrogenase I resistant to feed back inhibition by threonine;
the thrB gene which codes for homoserine kinase;
the thrc gene which codes for threonine synthase;
the rhtA gene which codes for a putative transmembrane protein;
the asd gene which codes for aspartate-α-semialdehyde dehydrogenase; and
the aspC gene which codes for aspartate aminotransferase (aspartate transaminase).

The sequence of the thrA gene of *Escherichia coli* which encodes aspartokinase homoserine dehydrogenase I has been elucidated (nucleotide positions 337 to 2799, GenBank accession NC_000913.2, gi: 49175990). The thrA gene is located between the thrL and thrB genes on the chromosome of *E. coli* K-12. The nucleotide sequence of the thrB gene of *Escherichia coli* which encodes homoserine kinase has been elucidated (nucleotide positions 2801 to 3733, GenBank accession NC_000913.2, gi: 49175990). The thrB gene is located between the thrA and thrC genes on the chromosome of *E. coli* K-12. The nucleotide sequence of the thrC gene of *Escherichia coli* which encodes threonine synthase has been elucidated (nucleotide positions 3734 to 5020, GenBank accession NC_000913.2, gi: 49175990). The thrC gene is located between the thrB gene and the yaax open reading frame on the chromosome of *E. coli* K-12. All three genes function together as a single threonine operon. To enhance the expression of the threonine operon, the attenuator region which affects the transcription can be removed from the operon (WO2005/049808, WO2003/097839).

The mutated thrA gene which encodes feedback-resistant aspartokinase homoserine dehydrogenase I, as well as the thrB and thrc genes can be obtained as one operon from the well-known plasmid pVIC40. This plasmid is present in the threonine producing *E. coli* strain VKPM B-3996, and is described in detail in U.S. Pat. No. 5,705,371.

The rhtA gene is at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and is located between the pexB and ompX genes. The sequence expressing a protein encoded by the ORF1 has been designated the rhtA gene (rht: resistance to homoserine and threonine). Also, the rhtA23 mutation is an A-for-G substitution at position-1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The nucleotide sequence of the asd gene of *E. coli* has already been elucidated (nucleotide positions 3572511 to 3571408, GenBank accession NC_000913.1, gi:16131307), and can be obtained by PCR (polymerase chain reaction; refer to White, T. J. et al., Trends Genet., 5, 185 (1989)) by utilizing primers based on the nucleotide sequence of the gene. The asd genes from other microorganisms can be obtained in a similar manner.

Also, the nucleotide sequence of the aspC gene of *E. coli* has already been elucidated (nucleotide positions 983742 to 984932, GenBank accession NC_000913.1, gi:16128895), and can be obtained by PCR. The aspC genes from other microorganisms can be obtained in a similar manner.

L-Cysteine-Producing Bacteria

Examples of parent strains for deriving L-cysteine-producing bacteria of the present invention include, but are not limited to, strains belonging to the genus *Escherichia*, such as *E. coli* JM15 which has been transformed with different cysE alleles coding for feedback-resistant serine acetyltransferases (U.S. Pat. No. 6,218,168, Russian patent application 2003121601), *E. coli* W3110 which over-expresses genes which encode proteins suitable for secreting toxic substances (U.S. Pat. No. 5,972,663), *E. coli* strains with decreased cysteine desulfohydrase activity (JP11155571A2); *E. coli* W3110 with increased activity of a positive transcriptional regulator for the cysteine regulon encoded by the cysB gene (WO0127307A1), and the like.

L-Leucine-Producing Bacteria

Examples of parent strains for deriving L-leucine-producing bacteria of the present invention include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); *E. coli* strains obtained by the genetic engineering method described in WO96/06926; *E. coli* H-9068 (JP 8-70879 A), and the like.

The bacterium of the present invention may be improved by enhancing the expression of one or more genes involved in L-leucine biosynthesis. Examples of these genes include those of the leuABCD operon, which preferably include a leuA gene which has been mutated so that it encodes isopropylmalate synthase which is resistant to feedback inhibition by L-leucine (U.S. Pat. No. 6,403,342). In addition, the bacterium of the present invention may be improved by enhancing the expression of one or more genes coding for proteins which excrete L-amino acids from the bacterial cell. Examples of such genes include the b2682 and b2683 genes (ygaZH genes) (EP 1239041 A2).

L-Histidine-Producing Bacteria

Examples of parent strains for deriving L-histidine-producing bacteria of the present invention include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* A180/pFM201 (U.S. Pat. No. 6,258,554) and the like.

Examples of parent strains for deriving L-histidine-producing bacteria of the present invention also include strains in which expression of one or more genes encoding an L-histidine biosynthetic enzyme are enhanced. Examples of these L-histidine-biosynthetic enzymes include ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the genes encoding the L-histidine biosynthetic enzyme (hisG, hisBHAFI) are inhibited by L-histidine, and therefore the L-histidine-producing ability can also be efficiently enhanced by introducing a mutation which induces resistance to the feedback inhibition into ATP phosphoribosyltransferase (hisG) (Russian Patent Nos. 2003677 and 2119536).

Specific examples of strains having an L-histidine-producing ability include *E. coli* FERM-P 5038 and 5048 which have been transformed with a vector carrying a DNA encoding an L-histidine-biosynthetic enzyme (JP 56-005099 A), *E. coli* strains transformed with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of parent strains for deriving L-glutamic acid-producing bacteria of the present invention include, but are not limited to, strains belonging to the genus *Escherichia*, such as *E. coli* VL334thrC$^+$ (EP 1172433). *E. coli* VL334 (VKPM B-1641) is auxotrophic for L-isoleucine and L-threonine and is mutated in the thrC and ilvA genes (U.S. Pat. No. 4,278,765). A wild-type allele of the thrc gene was transferred by general transduction using a bacteriophage P1 grown on the wild-type *E. coli* strain K12 (VKPM B-7). As a result, an L-isoleucine auxotrophic strain VL334thrC$^+$ (VKPM B-8961) was obtained.

Examples of parent strains for deriving the L-glutamic acid-producing bacteria of the present invention include, but are not limited to, strains in which expression of one or more genes encoding an L-glutamic acid biosynthetic enzyme are enhanced. Examples of the enzymes involved in L-glutamic acid biosynthesis include glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), and glucose phosphate isomerase (pgi).

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of parent strains for deriving the L-glutamic acid-producing bacteria of the present invention also include strains which have decreased or eliminated activity of an enzyme that catalyzes synthesis of a compound other than L-glutamic acid, and branches off from the L-glutamic acid biosynthesis pathway. Examples of such enzymes include isocitrate lyase, α-ketoglutarate dehydrogenase, phosphotransacetylase, acetate kinase, acetohydroxy acid synthase, acetolactate synthase, formate acetyltransferase, lactate dehydrogenase, and glutamate decarboxylase. Bacteria belonging to the genus *Escherichia* deficient in the α-ketoglutarate dehydrogenase activity or having a reduced α-ketoglutarate dehydrogenase activity and methods for obtaining them are described in U.S. Pat. Nos. 5,378,616 and 5,573,945.

Specifically, these strains include the following:

*E. coli* W3110sucA:Kmr
*E. coli* AJ12624 (FERM BP-3853)
*E. coli* AJ12628 (FERM BP-3854)
*E. coli* AJ12949 (FERM BP-4881)

*E. coli* W3110sucA:Kmr is obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacterium include those which belong to the genus *Escherichia* and have resistance to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FERM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria include mutant strains belonging to the genus *Pantoea* which are deficient in α-ketoglutarate dehydrogenase activity or have a decreased α-ketoglutarate dehydrogenase activity, and can be obtained as described above. Such strains include *Pantoea ananatis* AJ13356 (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and received an accession number of FERM BP-6615. *Pantoea ananatis* AJ13356 is deficient in α-ketoglutarate dehydrogenase activity as a result of the disruption of the αLKGDH-E1 subunit gene (sucA). The above strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-Phenylalanine-Producing Bacteria

Examples of parent strains for deriving L-phenylalanine-producing bacteria of the present invention include, but are not limited to, strains belonging to the genus *Escherichia*, such as *E. coli* AJ12739 (tyrA:Tn10, tyrR) (VKPM B-8197); *E. coli* HW1089 (ATCC 55371) harboring the pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407, 952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488-424 B1). Furthermore, L-phenylalanine producing bacteria belonging to the genus *Escherichia* which have an enhanced activity of the protein encoded by the yedA gene or the yddG gene may also be used (U.S. patent applications 2003/0148473 A1 and 2003/0157667 A1).

L-Tryptophan-Producing Bacteria

Examples of parent strains for deriving the L-tryptophan-producing bacteria of the present invention include, but are not limited to, strains belonging to the genus *Escherichia*, such as *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756, 345); *E. coli* SV164 (pGH5) having a serA allele encoding phosphoglycerate dehydrogenase resistant to feedback inhibition by serine and a trpE allele encoding anthranilate synthase resistant to feedback inhibition by tryptophan (U.S. Pat. No. 6,180,373); *E. coli* AGX17 (pGX44) (NRRL B-12263) and AGX6(pGX50) aroP (NRRL B-12264) deficient in the enzyme tryptophanase (U.S. Pat. No. 4,371,614); *E. coli* AGX17/pGX50, pACKG4-pps in which a phosphoenolpyruvate-producing ability is enhanced (WO9708333, U.S. Pat. No. 6,319,696), and the like may be used. Furthermore, L-tryptophan producing bacteria belonging to the genus *Escherichia* which have an enhanced activity of the protein encoded by the yedA gene or the yddG gene may also be used (U.S. patent applications 2003/0148473 A1 and 2003/0157667 A1).

Examples of parent strains for deriving the L-tryptophan-producing bacteria of the present invention also include strains in which one or more activities of the enzymes selected from anthranilate synthase (trpE), phosphoglycerate dehydrogenase (serA), and tryptophan synthase (trpAB) are enhanced. The anthranilate synthase and phosphoglycerate dehydrogenase are both subject to feedback inhibition by L-tryptophan and L-serine, so a mutation which results in desensitizing the feedback inhibition may be introduced into these enzymes. Specific examples of strains having such a mutation include an *E. coli* SV164 which harbors desensitized anthranilate synthase and a strain obtained by transforming the plasmid pGH5 into *E. coli* SV164 (WO 94/08031), which contains a serA gene which has been mutated so that it encodes feedback-desensitized phosphoglycerate dehydrogenase.

Examples of parent strains for deriving the L-tryptophan-producing bacteria of the present invention also include strains transformed with the tryptophan operon which contains a gene encoding desensitized anthranilate synthase (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of Ca and 13 subunits which are encoded by trpA and trpB, respectively. In addition, L-tryptophan-producing ability may be improved by enhancing expression of the isocitrate lyase-malate synthase operon (WO2005/103275).

L-Proline-Producing Bacteria

Examples of parent strains for deriving L-proline-producing bacteria of the present invention include, but are not limited to, strains belonging to the genus *Escherichia*, such as *E. coli* 702ilvA (VKPM B-8012) which is deficient in the ilvA gene and is able to produce L-proline (EP 1172433).

The bacterium of the present invention may be improved by enhancing the expression of one or more genes involved in L-proline biosynthesis. Examples of preferred genes for L-proline producing bacteria include the proB gene coding for glutamate kinase which is desensitized to feedback inhibition by L-proline (DE Patent 3127361). In addition, the bacterium of the present invention may be improved by enhancing the expression of one or more genes coding for proteins excreting L-amino acid from the bacterial cell. Such genes include the b2682 and b2683 genes (ygaZH genes) (EP1239041 A2).

Examples of bacteria belonging to the genus *Escherichia*, which have an activity to produce L-proline, include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15th Miami winter symposium, 1983, p. 34), and the like.

L-Arginine-Producing Bacteria

Examples of parent strains for deriving L-arginine-producing bacteria of the present invention include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which the argA gene encoding N-acetylglutamate synthetase is introduced (EP1170361A1), and the like.

Examples of parent strains for deriving L-arginine producing bacteria of the present invention also include strains in which expression of one or more genes encoding an L-arginine biosynthetic enzyme are enhanced. Examples of the L-arginine biosynthetic enzymes include N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Example of parent strains for deriving L-valine-producing bacteria of the present invention include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by the L-valine that is produced. Furthermore, the ilvA gene in the operon is desirably disrupted so that threonine deaminase activity is decreased. Examples of parent strains for deriving L-valine-producing bacteria of the present invention also include mutants of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 113545 Moscow, 1 Dorozhny Proezd.) on Jun. 24, 1988 under accession number VKPM B-4411.

Furthermore, mutants requiring lipoic acid for growth and/or lacking $H^+$-ATPase can also be used (WO96/06926).

L-Isoleucine-Producing Bacteria

Examples of parent strains for deriving L-isoleucine producing bacteria of the present invention include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used (JP 2-458 A, FR 0356739, and U.S. Pat. No. 5,998,178).

<1-2> Enhancement of the Iron Transporter Activity

The bacterium of the present invention can be obtained by modifying a bacterium having an L-amino acid-producing ability as described above so that the iron transporter activity is enhanced. However, the L-amino acid-producing ability may be imparted after the bacterium is modified so that the iron transporter activity is enhanced. As described below, the iron transporter activity can be enhanced by increasing the expression of a gene encoding a protein involved in the tonB system, which can be achieved by enhancing the expression of an endogenous gene by modifying an expression regulatory region such as a promoter, or enhancing expression of an exogenous gene by introducing a plasmid containing the gene, or the like. In addition, these methods may be combined.

In the present invention, the term "iron transporter" means a membrane protein which facilitates uptake of iron into the cellular cytoplasm, and the phrase "modifying so that the iron transporter activity is enhanced" includes when the number of iron transporter molecules per cell increases and when the iron transporter activity per molecule is improved as compared to a wild-type strain or unmodified strain. The iron transporter activity is improved not less than 150% per cell, preferably not less than 200%, more preferably not less than 300% per cell as compared to a wild-type strain or an unmodified strain. Examples of a wild-type strain belonging to the Enterobacteriaceae family which can be used as a control include *Escherichia coli* MG1655 strain (ATCC No. 47076), W3110 strain (ATCC No. 27325), and *Pantoea ananatis* AJ13355 strain (FERM BP-6615). The activity of the iron transporter can be determined by measuring the uptake of labeled $Fe^{3+}$ into the cells (J. Bacteriol, May. 2003 p 1870-1885).

The iron transporter activity can be enhanced by enhancing the expression of a gene encoding a protein involved in the tonB system. The enhanced expression as compared to a wild-type or unmodified strain can be confirmed by comparing the mRNA level of the gene of the tonB system to that of a wild-type or unmodified strain. Methods for confirming the expression of a gene include Northern hybridization and RT-PCR (Molecular cloning (Cold spring Harbor Laboratory Press, Cold spring Harbor (USA), 2001)). The expression may be any level as long as it is increased as compared to a wild-type or unmodified strain, and for example, the expression is preferably increased not less than 1.5-fold, more preferably not less than 2-fold, and further more preferably not less than 3-fold as compared to a wild-type or unmodified strain. Meanwhile, enhancing the expression of the gene of the tonB system may also be confirmed by an increase in the level of the corresponding protein as compared to a wild-type or unmodified strain, and the protein level may be detected, for example, by Western blotting using an antibody (Molecular cloning (Cold spring Harbor Laboratory Press, Cold spring Harbor (USA), 2001)).

Examples of the gene encoding a protein involved in the tonB system include the tonB gene, the fepA gene, and the fecA gene, or homologues thereof. The tonB system is a system for uptake of iron which is mediated by the membrane protein (TonB), and TonB also regulates the activities of the iron transporters (FepA and FecA) by transferring electrons to FepA and FecA (J. Bacteriol October 2001 vol. 183, No. 20, p 5885-5895). In the present invention, examples of a gene of *Escherichia coli* include the tonB gene of SEQ ID NO: 1 (nucleotide numbers 1309113 . . . 1309832 of GenBank Accession No. NC-000913), the fepA gene of SEQ ID NO: 3 (a complementary strand of nucleotide numbers 609477 . . . 611717 of GenBank Accession No. NC_000913), and the fecA gene of SEQ ID NO: 9 (a complementary strand of nucleotide numbers 4512376.451-4700 of GenBank Accession No. NC_000913.2).

In addition, the homologues of the above-mentioned *E. coli* genes can be obtained by cloning, based on homologies to the above-listed genes, from γ-proteobacterium that belongs to the genus *Escherichia, Enterobacter, Klebsiella, Serratia, Erwinia, Yersinia,* or the like; a coryneform bacterium such as *Corynebacterium glutamicum,* or *Brevibacterium lactofermentum,* a *Pseudomonas* bacterium such as *Pseudomonas aeruginosa*; a *Mycobacterium* bacterium such as *Mycobacterium tuberculosis*; or the like. The homologues may be amplified by PCR using, for example, synthetic oligonucleotides shown in SEQ ID NOS: 5 and 6 for the tonB gene, or SEQ ID NOS: 7 and 8 for the fepA gene.

The homologies between the amino acid sequences and nucleotide sequences can be determined by using the algorithm BLAST developed by Karlin and Altschul (Pro. Natl. Acad. Sci. USA, 90, 5873 (1993)) or the algorithm FASTA developed by Pearson (Methods Enzymol., 183, 63 (1990)). Based on the algorithm BLAST, programs called BLASTN and BLASTX have been developed (http://www.ncbi.nlm.nih.gov).

The phrase "homologue of the gene of the tonB system" indicates that a gene derived from other bacteria, or a naturally or artificially mutated gene, which has high structural similarity to the tonB gene, fepA gene, or fecA gene from *Escherichia coli* and is able to improve the iron transport activity when introduced or amplified in a host. The "homologues of the tonB gene, fepA gene, and fecA gene which are involved in the tonB system" include genes which encode a protein which has homology of at least 80%, preferably at least 90%, more preferably 95%, particularly preferably at least 98% to the entire sequence of SEQ ID NOS: 2 (tonB), 4 (fepA), or 10 (fecA), and is able to function as an iron transporter regulatory factor (tonB) or as an iron transporter (fepA or fecA). This function can be confirmed by expressing the gene in a host cell and examining the transport of iron through the cell membrane (see, the above-mentioned Non-patent documents 1 to 4). Alternatively, whether a gene is a homologue of the tonB gene, fepA gene, or fecA gene can be confirmed by preparing a strain in which the corresponding wild-type gene is disrupted and examining whether the gene can complement the function of the wild-type gene when introduced into the gene-disrupted strain, i.e., whether the introduced gene can restore iron uptake.

Meanwhile, the tonB gene, fepA gene, and/or fecA gene are not limited to their respective wild-type genes and may be mutants or artificially modified genes that encode proteins having the amino acid sequences of SEQ ID NO: 2, 4, or 10, but which may include substitution, deletion, insertion, or addition of one or several amino acids at one or a plurality of positions as long as the function of the TonB, FepA, and/or FecA proteins encoded by these genes is maintained, that is, the function as an iron transporter regulatory factor (TonB) or an iron transporter (FepA or FecA). In the present invention, although depending on the positions in the ternary structure and types of amino acid residues in the proteins, the term "one or several" specifically means 1 to 20, preferably 1 to 10, and more preferably 1 to 5. The above-mentioned substitution is preferably a conservative substitution, and examples of conservative substitutions include substitution between aromatic amino acids such as a substitution among Phe, Trp, and Tyr; substitution between hydrophobic amino acids such as a substitution among Leu, Ile, and Val; substitution between polar amino acids such as a substitution between Gln and Asn; substitution between basic amino acids such as a substitution among Lys, Arg, and His; substitution between acidic amino acids such as a substitution between Asp and Glu; substitution between amino acids having a hydroxyl group such as a substitution between Ser and Thr. Specific examples of a conservative substitution include substitution of Ser or Thr for Ala; substitution of Gln, His, or Lys for Arg; substitution of Glu, Gln, Lys, His, or Asp for Asn; substitution of Asn, Glu, or Gln for Asp; substitution of Ser or Ala for Cys; substitution of Asn, Glu, Lys, His, Asp, or Arg for Gln; substitution of Gly, Asn, Gln, Lys, or Asp for Glu; substitution of Pro for Gly; substitution of Asn, Lys, Gln, Arg, or Tyr for His; substitution of Leu, Met, Val, or Phe for Ile; substitution of Ile, Met, Val, or Phe for Leu; substitution of Asn, Glu, Gln, His, or Arg for Lys; substitution of Ile, Leu, Val, or Phe for Met; substitution of Trp, Tyr, Met, Ile, or Leu for Phe; substitution of Thr or Ala for Ser; substitution of Ser or Ala for Thr; substitution of Phe or Tyr for Trp; substitution of His, Phe, or Trp for Tyr; and substitution of Met, Ile, or Leu for Val. Meanwhile, the above-mentioned amino acid substitution, deletion, insertion, addition, or inversion may be a naturally occurring mutation (mutant or variant) due to an individual difference, a difference in types, or the like among the bacteria harboring the tonB gene, fepA gene, or fecA gene.

Meanwhile, the tonB gene, fepA gene, and fecA gene may each be a DNA which hybridizes with a nucleotide sequence complementary to SEQ ID NOS: 1, 3, and 9, respectively, or a probe that can be prepared from the sequence under stringent conditions, as long as the gene encodes a protein having a function as an iron transporter regulatory factor (tonB) or as an iron transporter (fepA or fecA). In the present invention, the term "stringent conditions" refers to conditions where a so-called specific hybrid is formed and non-specific hybrid is not formed. It is difficult to clearly define the conditions by a numerical value, and examples include conditions where DNAs having high homology, for example, DNAs having homology of at least 80%, preferably at least 90%, more preferably at least 95%, or particularly preferably at least 98% hybridize with each other and DNAs having homology of less than 80% do not hybridize with each other; and specific examples thereof include washing in general Southern hybridization, i.e., washing at the salt concentration of 1×SSC, 0.1% SDS, preferably 0.1×SSC, 0.1% SDS, at 60° C., preferably at 68° C., once, preferably twice or three times.

Expression of the above-mentioned tonB gene, fepA gene, and fecA gene can be increased by, for example, increasing the copy number of the genes in a cell using a gene recombination technique. For example, a DNA fragment containing the gene is ligated to a vector that functions in the host bacterium, preferably a multi-copy vector, to thereby prepare a recombinant DNA, and the recombinant DNA is used to transform the host bacterium.

When using the tonB gene and fepA gene of *Escherichia coli*, the tonB gene and fepA gene can be obtained by PCR (polymerase chain reaction; White, T. J. et al., Trends Genet. 5, 185 (1989)) using primers based on the nucleotide sequences of SEQ ID NOS: 1, or 3, for example, primers of SEQ ID NOS: 5 and 6 (tonB), or 7 and 8 (fepA) and a chromosomal DNA of *Escherichia coli* as the template. The tonB gene and fepA gene from another bacterium can also be obtained by PCR from the chromosomal DNA or genomic DNA library of the bacterium using, as primers, oligonucleotides prepared based on the known sequences of the tonB gene and fepA gene of the bacterium or of the tonB gene and fepA gene of another kind of bacterium, or the amino acid sequence of the TonB protein, and FepA protein; or by hybridization using an oligonucleotide prepared based on the sequence as a probe. A chromosomal DNA can be prepared from a bacterium that serves as a DNA donor by the method of Saito and Miura (Biochem. Biophys. Acta, 72, 619 (1963), Experiment Manual for Biotechnology, edited by The Society for Biotechnology, Japan, p 97-98, Baifukan Co., Ltd., 1992) or the like.

The fecA gene can be obtained in the same way.

Then, a recombinant DNA is prepared by ligating the tonB gene, fepA gene, or fecA gene which has been amplified by PCR to a vector DNA which is capable of functioning in the host bacterium. Examples of the vector capable of functioning in the host bacterium include vectors autonomously replicable in the host bacterium.

Examples of a vector which is autonomously replicable in *Escherichia coli* include pUC19, pUC18, pHSG299, pHSG399, pHSG398, pACYC184, (pHSG and pACYC are available from Takara Bio Inc.), RSF1010 (Gene vol. 75(2), p 271-288, 1989), pBR322, pMW219, pMW119 (pMW is available form Nippon Gene Co., Ltd.), pSTV28, and pSTV29 (Takara Bio Inc.). A phage DNA vector can also be used.

To ligate the gene to the above-mentioned vector, the vector is digested with a restriction enzyme corresponding to a recognition site in the terminus of a DNA fragment containing the tonB gene, fepA gene, and fecA gene. Ligation is generally performed using a ligase such as T4 DNA ligase. Methods of digesting and ligating DNA, preparation of a chromosomal DNA, preparation of a plasmid DNA, transformation, PCR, design of oligonucleotides to be used as primers are well known to the person skilled in the art. These methods are described in Sambrook, J., Fritsch, E. F., and Maniatis, T., "Molecular Cloning A Laboratory Manual, Second Edition", Cold Sprig Harbor Laboratory Press, (1989), and the like.

The thus-prepared recombinant DNA is introduced into a bacterium by a conventional transformation method, such as electroporation (Canadian Journal of Microbiology, 43, 197 (1997)). It is also possible to increase the DNA permeability by treating the recipient cells with calcium chloride, which has been reported for *Escherichia coli* K-12 (Mandel, M. and Higa, A., J. Mol. Biol., 53, 159 (1970), and introduce a DNA into a competent cell at the proliferation stage, which has been reported with *Bacillus subtilis* (Duncan, C. H., Wilson, G. A and Young, F. E, Gene, 1, 153 (1977)).

The copy number of the tonB gene, fepA gene, and fecA gene can also be increased by introducing multiple copies of the genes into the chromosomal DNA of the host bacterium. Introducing multiple copies of the genes into the chromosomal DNA of the host bacterium can be attained by homologous recombination using a target sequence present on the chromosomal DNA in multiple copies. This may be a repetitive DNA or an inverted repeat present on the edge of a transposing element. Alternatively, as disclosed in JP 2-109985 A, multiple copies of the tonB gene, fepA gene, and fecA gene can be introduced into the chromosomal DNA by inserting the gene into a transposon, and transferring it so that multiple copies of the gene are integrated into the chromosomal DNA. Integration of these genes into the chromosome can be confirmed by Southern hybridization using a portion of the genes as a probe.

Furthermore, expression of the tonB gene, fepA gene, and fecA gene may be enhanced by, as described in WO 00/18935, substituting an expression regulatory sequence such as the native promoter with a stronger promoter, whether the gene is present on the chromosome or a plasmid, amplifying a regulatory element that is able to increase expression of the genes, or deleting or attenuating a regulatory element that decreases expression of the genes. Examples of known strong promoters include the lac promoter, trp promoter, trc promoter, tac promoter, lambda phage PR promoter, PL promoter, and tet promoter (WO98/004715).

Furthermore, the native promoter of the tonB gene, fepA gene, and fecA gene can be strengthened by introducing nucleotide substitution into the promoter (EP1033407). A method to evaluate the strength of a promoter and examples of strong promoters are described in Goldstein et al. (Prokaryotic promoters in biotechnology. Biotechnol. Annu. Rev., 1995, 1, 105-128) or the like. In addition, it is known that a spacer sequence between the ribosome binding site (RBS) and the translation initiation codon, especially, several nucleotides just upstream of the initiation codon, has a great influence on translation efficiency. Therefore, this sequence may be modified.

In addition, to enhance the activity of a protein encoded by the tonB gene, fepA gene, and fecA gene, a mutation that increases the activity of the iron transporter regulatory factor or iron transporter may be introduced into the genes. Examples of such a mutation include a mutation in the promoter sequence to increase the transcription level of tonB gene, fepA gene and fecA gene, and a mutation in the coding region to increase the specific activities of the TonB, FepA, or FecA proteins. In addition, a mutation to enhance an activity of a protein that positively regulates the expression of these genes may be introduced into the gene encoding such a protein.

<2> Method of Producing L-Amino Acid

The method of producing an L-amino acid of the present invention is to culture the bacterium of the present invention in a medium to produce and accumulate an L-amino acid in the medium or bacterial cells, and collecting the L-amino acid from the medium or the bacterial cells.

Conventional media which are typically used in bacterial fermentative production of an L-amino acid can be used. That is, a general medium containing a carbon source, nitrogen source, inorganic ion, and if necessary, other organic components can be used. In the present invention, examples of the carbon source include sugars such as glucose, sucrose, lactose, galactose, fructose and a starch hydrolysate; alcohols such as glycerol and sorbitol; and organic acids such as fumaric acid, citric acid and succinic acid. Examples of the nitrogen source include inorganic ammonium salts such as ammonium sulfate, ammonium chloride and ammonium phosphate; an organic nitrogen such as a soybean hydrolysate; ammonia gas; and aqueous ammonia. As organic trace nutrients, auxotrophic substances such as vitamin B1 and L-homoserine, yeast extract, and the like are preferably contained in the medium in appropriate amounts. Besides such substances, if necessary, potassium phosphate, magnesium sulfate, iron ion, manganese ion, or the like may be added in small amounts. The medium to be used in the present invention may be a natural medium or a synthetic medium as long as it contains a carbon source, nitrogen source, inorganic ion, and if necessary, other organic trace nutrients.

The culture is preferably performed under aerobic conditions for 1 to 7 days at a temperature of 24° C. to 37° C. and a pH of 5 to 9. The pH can be adjusted with an inorganic or organic acidic or alkaline substance, ammonia gas or the like. The L-amino acid can be collected from the fermentation liquid by a conventional method such as ion-exchange resin, precipitation, and other known methods. When the L-amino acid accumulates in the bacterial cells, the L-amino acid can be collected, for example, by disrupting the bacterial cells by ultrasonication or the like to release the L-amino acid into the supernatant fraction, and then the bacterial cells are removed by centrifugation, followed by subjecting the resulting supernatant fraction to an ion-exchange resin or the like.

When producing a basic L-amino acid, fermentation may be performed while controlling the pH of the medium during culture to 6.5-9.0 and controlling the pH of the medium after completion of the culture to 7.2-9.0, as well as controlling the pressure in the fermentation tank during fermentation so that it is positive. Alternatively, carbon dioxide or a mixed gas containing carbon dioxide may be added to the medium so that a bicarbonate ion and/or carbonate ion are present in an amount of at least 2 g/L in the culture medium during the culture period. These ions function as counter ions against the cation of the basic L-amino acids, and the target basic L-amino acid can be collected (JP 2002-065287 A, WO2006/038695).

EXAMPLES

Hereinafter, the present invention will be described in more detail by referring to the following non-limiting examples. If not otherwise specified, all the reagents used were purchased from Wako Pure Chemical Industries, Ltd. or Nacalai Tesque, Inc. The compositions of the media to be used in the Examples are shown below. The pH of each medium was adjusted with NaOH or HCl.

(L Medium)

| | |
|---|---|
| Bacto-tryptone (manufactured by Difco) | 10 g/L |
| Yeast extract (manufactured by Difco) | 5 g/L |
| Sodium chloride | 10 g/L |
| pH 7.0 | |

The medium was sterilized by steam at 120° C. for 20 minutes.

[L Agar Medium]

| L medium | |
|---|---|
| Bacto-agar | 15 g/L |

The medium was sterilized by steam at 120° C. for 20 minutes.

[L-lysine production medium for *Escherichia* bacteria]

| | |
|---|---|
| Glucose | 40 g/L |
| Ammonium sulfate | 24 g/L |
| Potassium dihydrogen phosphate | 1.0 g/L |
| Magnesium sulfate heptahydrate | 1.0 g/L |
| Iron sulfate heptahydrate | 0.01 g/L |
| Manganese sulfate heptahydrate | 0.01 g/L |
| Yeast extract | 2.0 g/L |
| Calcium carbonate (Official grade) | 50 g/L (separately sterilized) |

The medium was adjusted to pH 7.0 with potassium hydroxide and sterilized by steam at 115° C. for 10 minutes.

Glucose and magnesium sulfate heptahydrate were separately sterilized.

Calcium carbonate (Official grade) was separately sterilized by heating at 180° C.

Chloramphenicol (25 mg/L) and ampicillin (100 mg/L) were added before culture as antibiotics.

[L-Threonine Production Medium for *Escherichia* Bacteria]

| | |
|---|---|
| Glucose | 40 g/L |
| Ammonium sulfate | 16 g/L |
| Potassium dihydrogen phosphate | 1.0 g/L |
| Magnesium sulfate heptahydrate | 1.0 g/L |
| Iron sulfate (IV) heptahydrate | 0.01 g/L |
| Manganese sulfate (IV) heptahydrate | 0.01 g/L |
| Calcium carbonate (Official grade) | 30 g/L (separately sterilized) |

The medium was adjusted to pH 7.5 with potassium hydroxide and sterilized at 115° C. for 10 minutes.

Glucose and magnesium sulfate heptahydrate were separately sterilized.

Calcium carbonate (Official grade) was separately sterilized by heating at 180° C.

Streptomycin (100 mg/L) and ampicillin (100 mg/L) were added before culture as antibiotics.

Example 1

<1> Construction of a Plasmid for Amplifying the tonB Gene or the fepA Gene

To evaluate an effect of independent amplification of the tonB gene, and fepA gene on production of L-lysine, plasmid vectors for amplifying each of the genes were constructed. The entire chromosomal nucleotide sequence of *Escherichia coli* (*Escherichia coli* K-12 strain) has been disclosed (Science, 277, 1453-1474 (1997)), and primers to amplify the tonB gene and fepA gene were designed based on the nucleotide sequences of the tonB gene (nucleotide numbers 1309113-1309832 of GenBank Accession No. NC_000913: SEQ ID NO: 1), and fepA gene (complementary strand of nucleotide numbers 609477-611717 of NCBI Accession No. NC_000913: SEQ ID NO: 3). SEQ ID NOS: 5 to 8 (for tonB: SEQ ID NOS: 5 and 6; for fepA: SEQ ID NOS: 7 and 8) represent primers to amplify the genes. These primers were used to perform PCR using the chromosomal DNA of *Escherichia coli* MG1655 strain as a template. The chromosomal DNA was obtained using Bacterial Genomic DNA purification kit (Edge Bio Systems). PCR was performed using pyrobest DNA polymerase (manufactured by Takara Bio Inc.) such that a cycle of 96° C. for 20 seconds, 65° C. for 20 seconds, and 72° C. for 2 minutes was repeated 25 cycles.

The amplified tonB gene and fepA gene were purified and ligated to SmaI-digested vectors, pSTV28 (manufactured by Takara Bio Inc.) and pMW119 (manufactured by Nippon Gene Co., Ltd.), respectively, to thereby obtain a plasmid for amplifying the tonB gene (pStonB), and a plasmid for amplifying the fepA gene (pSfepA).

Example 2

Construction of a Strain in which the Lysine Decarboxylase-Encoding Genes (cadA and ldcC) are Disrupted A strain which produces no lysine decarboxylase was constructed. The lysine decarboxylases are encoded by the cadA gene (Genbank Accession No. NP_418555, SEQ ID NO: 17) and the ldcC gene (Genbank Accession No. NP_414728, SEQ ID NO: 11) (WO 96/17930). WC196 (FERM BP-5252) was the parent strain.

The cadA gene and the ldcC gene were disrupted by the method developed by Datsenko and Wanner, which is called "Red-driven integration" (Proc. Natl. Acad. Sci. USA, 2000, vol. 97, No. 12, p 6640-6645) and by an excision system derived from λ phage (J. Bacteriol. 2002 September; 184(18): 5200-3. Interactions between integrase and excisionase in the phage lambda excisive nucleoprotein complex. Cho E H, Gumport R I, Gardner J F.). "Red-driven integration" makes it possible to construct a gene-disrupted strain in one step by employing a PCR product obtained by using as primers synthetic oligonucleotides designed to have a part of the targeted gene on the 5'-ends and a part of an antibiotic-resistance gene on the 3'-ends. Combining the λ phage-derived excision system permits the removal of the antibiotic-resistance gene that has been incorporated into the gene-disrupted strain (WO2005/010175).

(1) Disruption of the cadA Gene

The pMW118-attL-Cm-attR plasmid (WO2005/010175) was used as a template for PCR. pMW118-attL-Cm-attR was obtained by inserting the attL and attR genes, which are attachment sites for λ phage, and the cat gene, which is an antibiotic resistance gene, into pMW118 (Takara Bio Inc.) The genes are arranged in the following order: attL-cat-attR.

PCR was performed using, as primers, the synthetic oligonucleotides shown in SEQ ID NOS: 13 and 14, which have sequences corresponding to attL and attR on the 3'-ends and a sequence corresponding to a part of the targeted cadA gene on the 5'-ends.

The amplified PCR product was purified on an agarose gel and introduced into the *Escherichia coli* WC1-96 strain by electroporation. This strain harbors pKD46 which has temperature-sensitive replicability. pKD46 (Proc. Natl. Acad. Sci. USA, 2000, vol. 97, No. 12, p 6640-6645) contains a DNA fragment of 2,154 nucleotides derived from λ phage which contains the Red recombinase-encoding genes (γ, β, and exo genes) of the λ Red homologous recombination system, which is controlled by an arabinose-inducible ParaB promoter (GenBank/EMBL Accession No. J02459, nucleotide numbers 31088 to 33241). pKD46 is necessary to integrate the PCR product into the chromosome of the WC1-96 strain.

Competent cells for electroporation were prepared as follows. That is, cells of the *Escherichia coli* WC1-96 strain were cultured overnight at 30° C. in LB medium containing 100 mg/L ampicillin, and then diluted 100-fold with 5 mL of SOB medium (Molecular Cloning: Laboratory manual, 2nd edition, Sambrook, J. et al., Cold Spring Harbor Laboratory Press (1989)) containing ampicillin (20 mg/L) and L-arabinose (1 mM). The diluted cells were grown with aeration at 30° C. until the OD600 reached about 0.6, and then concentrated 100-fold and washed three times with 10% glycerol so that the cells were available for electroporation. The electroporation was performed with 70 μL of the competent cells and about 100 ng of the PCR product. After the electroporation, 1 mL of SOC medium (Molecular Cloning: Laboratory manual, 2nd edition, Sambrook, J. et al., Cold Spring Harbor Laboratory Press (1989)) was added to the cells, and cells were cultured at 37° C. for 2.5 hours, and then subjected to plate culture onto L-agar medium containing Cm (chloramphenicol) (25 mg/L), to thereby select Cm-resistant recombinant strains. Subsequently, to remove the plasmid pKD46, the cells were subcultured twice at 42° C. on L-agar medium containing Cm, and ampicillin resistance of the resultant colonies were examined, to thereby yield ampicillin-sensitive strains in which the pKD46 was cured.

Deletion of the cadA gene in the mutant strain, which had been identified by the chloramphenicol-resistance gene, was confirmed by PCR. The cadA-disrupted strain was named WC196ΔcadA:att-cat.

Subsequently, the helper plasmid pMW-intxis-ts (WO2005/010175) was used to remove the att-cat gene which had been introduced into the cadA gene. The plasmid pMW-intxis-ts carries a gene encoding the integrase (Int) of λ phage, and the gene encoding excisionase (Xis), and has temperature-sensitive replicability.

Competent cells of the WC196ΔcadA:att-cat strain were prepared by a conventional method, and were then transformed with the helper plasmid pMW-intxis-ts, and then subjected to plate culture at 30° C. onto L-agar medium containing 50 mg/L ampicillin, to thereby select ampicillin-resistant strains.

Subsequently, to remove the plasmid pMW-intxis-ts, the cells were subcultured twice at 42° C. on L-agar medium, and ampicillin resistance and chloramphenicol resistance of the resulting colonies were examined, to thereby yield a chloramphenicol and ampicillin-sensitive strain, in which the cadA gene was disrupted, and att-cat and the pMW-intxis-ts were removed. The strain was named WC196ΔcadA.

(2) Disruption of the ldcC Gene in the WC196ΔcadA Strain

The ldcC gene in the WC196ΔcadA strain was disrupted by using oligonucleotides of SEQ ID NOS: 15 and 16 as primers in the same way as described above. In this way, a cadA and ldcC-disrupted strain named WC196ΔcadAΔldcC was obtained.

<2> Introduction of a Plasmid for Lysine Production into the WC196ΔcadAΔldcC Strain WC196ΔcadAΔldcC strain was transformed with a plasmid for lysine production named pCABD2 (WO 01/53459), which carries the dapA gene, dapB gene, lysC gene and ddh gene, to thereby yield the WC196ΔcadAΔldcC/pCABD2 strain (WC196LC/pCABD2).

<2-2> Effect of Amplification of the tonB Gene in an L-Lysine-Producing Strain of Escherichia Bacterium The WC196LC/pCABD2 strain was transformed with the plasmid for amplifying the tonB gene (pStonB) which was constructed in Example 1 and a control plasmid (pSTV28) (Takara Bio Inc), and chloramphenicol-resistant strains were selected. Introduction of the plasmids was confirmed, and the pStonB-introduced strain and pSTV28-introduced strain were named WC196LC/pCABD2/pStonB strain and WC196LC/pCABD2/pSTV28 strain, respectively.

WC196LC/pCABD2/pStonB strain and WC196LC/pCABD2/pSTV28 strain were cultured at 37° C. in L-medium containing 50 mg/L chloramphenicol until the final OD600 reached about 0.6, and then an equal volume of 40% glycerol solution was added to the culture, followed by stirring. Then, the resulting suspension was dispensed in appropriate amounts and stored at −80° C., which was used as a glycerol stock.

The glycerol stocks of the strains were thawed, and 100 μL of each strain was uniformly applied on an L-plate containing 25 mg/L chloramphenicol and 20 mg/L streptomycin, and cultured at 37° C. for 24 hours. The bacterial cells growing on the plate were suspended in 2-3 mL of a fermentation medium so that OD620 became 13.5, and 1 mL of the suspension was inoculated into 20 mL of the fermentation medium (L-lysine production medium for Escherichia bacteria) containing 25 mg/L chloramphenicol and 20 mg/L streptomycin in a 500 mL-Sakaguchi flask and cultured at 37° C. using a reciprocal shaker for 48 hours. The amount of L-lysine which accumulated in the medium was determined using a Biotech Analyzer AS210 (Sakura Seiki Co. Ltd.).

Table 1 shows the amounts of L-lysine present after 24 hours. In the case of the WC196LC/pCABD2/pStonB strain, the amount of L-lysine present 24 hours later was higher as compared to the WC196LC/pCABD2/pSTV28 strain, which did not contain the tonB gene. This data shows that the L-lysine-producing ability was improved by enhancing the expression of the tonB gene.

TABLE 1

| Bacterial strain | L-lysine (g/L) present after 24 hours |
| --- | --- |
| WC196LC/pCABD2/pSTV28 | 7.0 |
| WC196LC/pCABD2/pStonB | 9.5 |

<2-3> Effect of Amplification of the fepA Gene in L-Lysine Producing Strain of Escherichia Bacterium WC196LC/pCABD2 strain was transformed with the plasmid for amplifying fepA gene (pSfepA) which was constructed in Example 1, and an ampicillin-resistant strain was selected. Introduction of the plasmid pSfepA was confirmed, and the pSfepA-introduced strain was named WC196LC/pCABD2/pSfepA.

In the same way as <2-2>, glycerol stocks of WC196LC/pCABD2/pSfepA strain and WC196LC/pCABD2 strain as a control were prepared. Here, 100 mg/L ampicillin was used instead of 50 mg/L chloramphenicol.

The glycerol stocks of these strains were thawed, and 100 μL of each of the strains was uniformly applied on an L-plate containing 100 mg/L ampicillin and 20 mg/L streptomycin, followed by culture at 37° C. for 24 hours. The bacterial cells which grew on the plate were collected and inoculated into the fermentation medium in the same way as <2-2> except that 100 mg/L ampicillin was used instead of 50 mg/L chloramphenicol, and the culture was performed over 24 hours, followed by determination of the L-lysine amount using a Biotech Analyzer AS210 (Sakura Seiki Co., Ltd.).

Table 2 shows the amount of L-lysine which was present after 24 hours. For the WC196LC/pCABD2/pSfepA strain, the amount of L-lysine present after 24 hours was higher as compared to the WC196LC/pCABD2 strain, which did not contain the fepA gene, which revealed that the L-lysine-producing ability was improved by enhancing the expression of the fepA gene.

TABLE 2

| Bacterial strain | L-lysine (g/L) present after 24 hours |
| --- | --- |
| WC196LC/pCABD2 | 7.3 |
| WC196LC/pCABD2/pSfepA | 9.6 |

Example 3

Effect of Amplification of the fepA Gene in L-Threonine-Producing Strain of *Escherichia* Bacterium B-5318 strain was used as an L-threonine-producing strain. B-5318 strain has been deposited in Russian National Collection of Industrial Microorganisms (VKPM), GNII Genetika) on May 3, 1990, under accession No. VKPM B-5318. Construction of a fepA gene-amplified strain from the L-threonine producing bacterium was performed using the plasmid pSfepA which was constructed in Example 1.

The B-5318 strain was transformed with the plasmid pSfepA, and an ampicillin-resistant strain was selected. Introduction of the plasmid was confirmed, and the pSfepA-introduced strain was named B5318/pSfepA.

The B5318/pSfepA strain, and the B5318/pMW strain into which a control plasmid was introduced were cultured at 37° C. in an L-medium containing 100 mg/L ampicillin and 100 mg/L streptomycin until the final OD600 reached about 0.6, and then an equal volume of 40% glycerol solution was added to the obtained culture, followed by stirring. Then, the mixture was dispensed in appropriate amounts and stored in glycerol at −80° C., which was used as a glycerol stock.

The glycerol stocks of the strains were thawed, and 100 µL of each of the strains was uniformly applied on an L-plate containing 100 mg/L ampicillin and 100 mg/L streptomycin, and cultured at 37° C. for 24 hours. The bacterial cells growing on the plate were suspended in 6 mL of physiological saline so that OD620 became 3.0, and 0.5 mL of each of the suspensions was inoculated into 20 mL of the fermentation medium (L-threonine-producing medium for *Escherichia* bacteria) containing 100 mg/L ampicillin and 100 mg/L streptomycin in a 500 mL-Sakaguchi flask, and cultured at 37° C. for 24 hours using a reciprocal shaker. After the culture, the amount of L-threonine which had accumulated in the medium was determined using high performance liquid chromatography.

Table 3 shows the amount of L-threonine present after 24 hours. For the B5318/pSfepA strain, the amount of L-threonine was higher as compared to the B5318/pMW strain, which revealed that the productivity of L-threonine was improved by enhancing the expression of the fepA gene.

TABLE 3

| Bacterial strain | L-threonine (g/L) present after 24 hours |
|---|---|
| B5318/pMW | 4.22 |
| B5318/pSfepA | 4.87 |

INDUSTRIAL APPLICABILITY

Use of the bacterium of the present invention enables efficient fermentative production of basic L-amino acids such as L-lysine, L-ornithine, L-arginine, L-histidine and L-citrulline; aliphatic L-amino acids such as L-isoleucine, L-alanine, L-valine, L-leucine and L-glycine; hydroxy monoaminocarboxylic acids such as L-threonine and L-serine; cyclic L-amino acid such as L-proline; aromatic L-amino acids such as L-phenylalanine, L-tyrosine and L-tryptophan; sulfur-containing L-amino acids such as L-cysteine, L-cystine and L-methionine; and acidic L-amino acids such as L-glutamic acid, L-aspartic acid, L-glutamine and L-asparagine.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

---

The invention claimed is:

1. A method of producing an L-amino acid comprising culturing an L-amino acid-producing bacterium belonging to the Enterobacteriaceae family in a medium, and collecting the L-amino acid from the medium or said bacterium, wherein said bacterium has been modified to enhance the expression of a gene encoding a protein of the tonB system, wherein said gene is tonB, wherein said L-amino acid is selected from the group consisting of L-lysine and L-threonine, wherein said tonB gene encodes a protein comprising an amino acid sequence which is at least 95% identical to the entire sequence of SEQ ID NO: 2.

2. The method according to claim 1, wherein the expression is enhanced by a method selected from the group consisting of:
   a) increasing the copy number of said gene,
   b) modifying an expression regulatory sequence of said gene, and
   c) combinations thereof.

3. The method according to claim 1, wherein said tonB encodes a protein selected from the group consisting of:
   a) a protein comprising the amino acid sequence of SEQ ID NO: 2, and
   b) a protein comprising the amino acid sequence of SEQ ID NO: 2, wherein said sequence includes substitutions, deletions, insertions, or additions of one to 10 amino acids and wherein said protein is able to regulate the activity of the iron transporter.

4. The method according to claim 1, wherein said tonB is selected from the group consisting of:
   a) a DNA comprising the nucleotide sequence of SEQ ID NO: 1, and
   b) a DNA that hybridizes with a nucleotide sequence which is complementary to the nucleotide sequence of SEQ ID NO: 1 under stringent conditions comprising washing at a salt concentration of 0.1×SSC, 0.1% SDS, at 60° C., and said DNA encodes a protein that is able to regulate the activity of the iron transporter.

5. The method according to claim 1, wherein said bacterium belongs to the genus *Escherichia, Pantoea*, or *Enterobacter*.

6. The method according to claim 1, wherein said bacterium is *Escherichia coli*.

* * * * *

UNITED STATES PATENT AND TRADEMARK OFFICE
CERTIFICATE OF CORRECTION

| | | |
|---|---|---|
| PATENT NO. | : 8,765,407 B2 | Page 1 of 1 |
| APPLICATION NO. | : 12/179988 | |
| DATED | : July 1, 2014 | |
| INVENTOR(S) | : Iyo et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 502 days.

Signed and Sealed this
Twenty-second Day of March, 2016

Michelle K. Lee
*Director of the United States Patent and Trademark Office*

SEQUENCE LISTING

```
<160> NUMBER OF SEQ ID NOS: 18

<210> SEQ ID NO 1
<211> LENGTH: 720
<212> TYPE: DNA
<213> ORGANISM: Escherichia coli
<220> FEATURE:
<221> NAME/KEY: CDS
<222> LOCATION: (1)..(717)

<400> SEQUENCE: 1 atg acc ctt gat tta cct cgc cgc ttc ccc tgg ccg acg tta ctt tcg      48
Met Thr Leu Asp Leu Pro Arg Arg Phe Pro Trp Pro Thr Leu Leu Ser
1               5                   10                  15 gtc tgc att cat ggt gct gtt gtg gcg ggt ctg ctc tat acc tcg gta      96
Val Cys Ile His Gly Ala Val Val Ala Gly Leu Leu Tyr Thr Ser Val
                20                  25                  30 cat cag gtt att gaa cta cct gcg cct gcg cag ccg att tct gtc acg     144
His Gln Val Ile Glu Leu Pro Ala Pro Ala Gln Pro Ile Ser Val Thr
            35                  40                  45 atg gtt acg cct gct gat ctc gaa ccg cca caa gcc gtt cag ccg cca     192
Met Val Thr Pro Ala Asp Leu Glu Pro Pro Gln Ala Val Gln Pro Pro
        50                  55                  60 ccg gag ccg gtg gta gag cca gaa ccg gaa cct gag ccg atc ccc gaa     240
Pro Glu Pro Val Val Glu Pro Glu Pro Glu Pro Glu Pro Ile Pro Glu
65                  70                  75                  80
```

```
ccg cca aaa gaa gca ccg gtg gtc att gaa aag ccg aag ccg aaa cct     288
Pro Pro Lys Glu Ala Pro Val Val Ile Glu Lys Pro Lys Pro Lys Pro
                85                  90                  95 aag cca aaa ccg aag ccg gtg aaa aag gta cag gag cag cca aaa cgc     336
Lys Pro Lys Pro Lys Pro Val Lys Lys Val Gln Glu Gln Pro Lys Arg
            100                 105                 110 gat gtc aaa ccc gta gag tcg cgt ccg gca tca ccg ttt gaa aat acg     384
Asp Val Lys Pro Val Glu Ser Arg Pro Ala Ser Pro Phe Glu Asn Thr
        115                 120                 125 gca ccg gca cgc ctg aca tca agt aca gca acg gct gca acc agc aag     432
Ala Pro Ala Arg Leu Thr Ser Ser Thr Ala Thr Ala Ala Thr Ser Lys
    130                 135                 140 ccg gtt acc agt gtg gct tca gga cca cgc gca tta agc cgt aat cag     480
Pro Val Thr Ser Val Ala Ser Gly Pro Arg Ala Leu Ser Arg Asn Gln
145                 150                 155                 160 ccg cag tat ccg gca cga gca cag gca ttg cgc att gaa ggg cag gtt     528
Pro Gln Tyr Pro Ala Arg Ala Gln Ala Leu Arg Ile Glu Gly Gln Val
                165                 170                 175 aaa gtt aaa ttt gac gtt acg ccg gat ggt cgc gtg gat aac gta caa     576
Lys Val Lys Phe Asp Val Thr Pro Asp Gly Arg Val Asp Asn Val Gln
            180                 185                 190 atc ctc tca gcc aag cct gcg aac atg ttt gag cgt gag gtg aaa aat     624
Ile Leu Ser Ala Lys Pro Ala Asn Met Phe Glu Arg Glu Val Lys Asn
        195                 200                 205 gcg atg cgc aga tgg cgt tat gag ccg ggt aag cca ggc agt ggg att     672
Ala Met Arg Arg Trp Arg Tyr Glu Pro Gly Lys Pro Gly Ser Gly Ile
    210                 215                 220 gtg gtg aat atc ctg ttt aaa att aac ggc acc acc gaa att cag taa     720
Val Val Asn Ile Leu Phe Lys Ile Asn Gly Thr Thr Glu Ile Gln
225                 230                 235

<210> SEQ ID NO 2
<211> LENGTH: 239
<212> TYPE: PRT
<213> ORGANISM: Escherichia coli

<400> SEQUENCE: 2

Met Thr Leu Asp Leu Pro Arg Arg Phe Pro Trp Pro Thr Leu Leu Ser
1               5                   10                  15

Val Cys Ile His Gly Ala Val Ala Gly Leu Leu Tyr Thr Ser Val
            20                  25                  30

His Gln Val Ile Glu Leu Pro Ala Pro Ala Gln Pro Ile Ser Val Thr
        35                  40                  45

Met Val Thr Pro Ala Asp Leu Glu Pro Gln Ala Val Gln Pro Pro
    50                  55                  60

Pro Glu Pro Val Val Glu Pro Glu Pro Glu Pro Ile Pro Glu
65                  70                  75                  80

Pro Pro Lys Glu Ala Pro Val Val Ile Glu Lys Pro Lys Pro Lys Pro
                85                  90                  95

Lys Pro Lys Pro Lys Pro Val Lys Lys Val Gln Glu Gln Pro Lys Arg
            100                 105                 110

Asp Val Lys Pro Val Glu Ser Arg Pro Ala Ser Pro Phe Glu Asn Thr
        115                 120                 125

Ala Pro Ala Arg Leu Thr Ser Ser Thr Ala Thr Ala Ala Thr Ser Lys
    130                 135                 140

Pro Val Thr Ser Val Ala Ser Gly Pro Arg Ala Leu Ser Arg Asn Gln
145                 150                 155                 160

Pro Gln Tyr Pro Ala Arg Ala Gln Ala Leu Arg Ile Glu Gly Gln Val
```

```
                       165                 170                 175
Lys Val Lys Phe Asp Val Thr Pro Asp Gly Arg Val Asp Asn Val Gln
            180                 185                 190

Ile Leu Ser Ala Lys Pro Ala Asn Met Phe Glu Arg Glu Val Lys Asn
        195                 200                 205

Ala Met Arg Arg Trp Arg Tyr Glu Pro Gly Lys Pro Gly Ser Gly Ile
    210                 215                 220

Val Val Asn Ile Leu Phe Lys Ile Asn Gly Thr Thr Glu Ile Gln
225                 230                 235

<210> SEQ ID NO 3
<211> LENGTH: 2241
<212> TYPE: DNA
<213> ORGANISM: Escherichia coli
<220> FEATURE:
<221> NAME/KEY: CDS
<222> LOCATION: (1)..(2238)

<400> SEQUENCE: 3
```

| | | | | | | | | | | | | | | | | |
|---|---|---|---|---|---|---|---|---|---|---|---|---|---|---|---|---|
| atg | aac | aag | aag | att | cat | tcc | ctg | gcc | ttg | ttg | gtc | aat | ctg | ggg | att | 48 |
| Met | Asn | Lys | Lys | Ile | His | Ser | Leu | Ala | Leu | Leu | Val | Asn | Leu | Gly | Ile | |
| 1 | | | | 5 | | | | | 10 | | | | | 15 | | |
| tat | ggg | gta | gcg | cag | gca | caa | gag | ccg | acc | gat | act | cct | gtt | tca | cat | 96 |
| Tyr | Gly | Val | Ala | Gln | Ala | Gln | Glu | Pro | Thr | Asp | Thr | Pro | Val | Ser | His | |
| | | | 20 | | | | | 25 | | | | | 30 | | | |
| gac | gat | act | att | gtc | gtt | acc | gcc | gcc | gag | cag | aac | tta | cag | gcg | cct | 144 |
| Asp | Asp | Thr | Ile | Val | Val | Thr | Ala | Ala | Glu | Gln | Asn | Leu | Gln | Ala | Pro | |
| | | 35 | | | | | 40 | | | | | 45 | | | | |
| ggc | gtt | tcg | acc | atc | acc | gca | gat | gaa | atc | cgc | aaa | aac | ccg | gtt | gcc | 192 |
| Gly | Val | Ser | Thr | Ile | Thr | Ala | Asp | Glu | Ile | Arg | Lys | Asn | Pro | Val | Ala | |
| | 50 | | | | | 55 | | | | | 60 | | | | | |
| cgc | gat | gtg | tcg | aag | atc | atc | cgt | acc | atg | cca | ggc | gtt | aac | ctg | acc | 240 |
| Arg | Asp | Val | Ser | Lys | Ile | Ile | Arg | Thr | Met | Pro | Gly | Val | Asn | Leu | Thr | |
| 65 | | | | | 70 | | | | | 75 | | | | | 80 | |
| ggt | aac | tcc | acc | agt | ggt | cag | cgt | ggg | aat | aac | cga | cag | att | gat | att | 288 |
| Gly | Asn | Ser | Thr | Ser | Gly | Gln | Arg | Gly | Asn | Asn | Arg | Gln | Ile | Asp | Ile | |
| | | | | 85 | | | | | 90 | | | | | 95 | | |
| cgc | ggt | atg | ggt | ccg | gaa | aac | acg | ctg | att | ttg | att | gac | ggc | aag | ccg | 336 |
| Arg | Gly | Met | Gly | Pro | Glu | Asn | Thr | Leu | Ile | Leu | Ile | Asp | Gly | Lys | Pro | |
| | | | 100 | | | | | 105 | | | | | 110 | | | |
| gta | agc | agc | cgt | aac | tcg | gtg | cgt | cag | ggc | tgg | cgt | ggc | gag | cgc | gat | 384 |
| Val | Ser | Ser | Arg | Asn | Ser | Val | Arg | Gln | Gly | Trp | Arg | Gly | Glu | Arg | Asp | |
| | | 115 | | | | | 120 | | | | | 125 | | | | |
| acc | cgt | ggt | gat | act | tcc | tgg | gtg | cca | cct | gaa | atg | att | gaa | cgt | att | 432 |
| Thr | Arg | Gly | Asp | Thr | Ser | Trp | Val | Pro | Pro | Glu | Met | Ile | Glu | Arg | Ile | |
| | 130 | | | | | 135 | | | | | 140 | | | | | |
| gaa | gtt | ctg | cgt | ggt | ccg | gca | gct | gcg | cgt | tat | ggc | aac | ggc | gcg | gcg | 480 |
| Glu | Val | Leu | Arg | Gly | Pro | Ala | Ala | Ala | Arg | Tyr | Gly | Asn | Gly | Ala | Ala | |
| 145 | | | | | 150 | | | | | 155 | | | | | 160 | |
| ggc | ggc | gtg | gtt | aac | atc | att | acc | aaa | aaa | ggc | agc | ggc | gag | tgg | cac | 528 |
| Gly | Gly | Val | Val | Asn | Ile | Ile | Thr | Lys | Lys | Gly | Ser | Gly | Glu | Trp | His | |
| | | | | 165 | | | | | 170 | | | | | 175 | | |
| ggc | tcc | tgg | gac | gca | tat | ttc | aat | gcg | cca | gaa | cat | aaa | gag | gaa | ggt | 576 |
| Gly | Ser | Trp | Asp | Ala | Tyr | Phe | Asn | Ala | Pro | Glu | His | Lys | Glu | Glu | Gly | |
| | | | 180 | | | | | 185 | | | | | 190 | | | |
| gcc | acc | aaa | cgc | act | aac | ttt | agc | ctg | acc | ggt | ccg | ctg | ggc | gac | gaa | 624 |
| Ala | Thr | Lys | Arg | Thr | Asn | Phe | Ser | Leu | Thr | Gly | Pro | Leu | Gly | Asp | Glu | |
| | | 195 | | | | | 200 | | | | | 205 | | | | |
| ttc | agc | ttc | cgt | ttg | tat | ggc | aac | ctc | gac | aaa | acc | cag | gct | gac | gcg | 672 |
| Phe | Ser | Phe | Arg | Leu | Tyr | Gly | Asn | Leu | Asp | Lys | Thr | Gln | Ala | Asp | Ala | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 210 |     |     |     | 215 |     |     |     | 220 |     |     |     |     |     |      |
| tgg | gat | atc | aac | cag | ggc | cat | cag | tcc | gcg | cgt | gcc | gga | acg | tat | gcc | 720  |
| Trp | Asp | Ile | Asn | Gln | Gly | His | Gln | Ser | Ala | Arg | Ala | Gly | Thr | Tyr | Ala |      |
| 225 |     |     |     | 230 |     |     |     |     | 235 |     |     |     |     | 240 |     |      |
| acg | acg | tta | cca | gcc | ggg | cgc | gaa | ggg | gta | atc | aac | aaa | gat | att | aat | 768  |
| Thr | Thr | Leu | Pro | Ala | Gly | Arg | Glu | Gly | Val | Ile | Asn | Lys | Asp | Ile | Asn |      |
|     |     |     |     |     | 245 |     |     |     |     | 250 |     |     |     |     | 255 |      |
| ggc | gtg | gtg | cgc | tgg | gat | ttc | gcg | cca | ttg | caa | tcg | ctg | gaa | ctg | gaa | 816  |
| Gly | Val | Val | Arg | Trp | Asp | Phe | Ala | Pro | Leu | Gln | Ser | Leu | Glu | Leu | Glu |      |
|     |     |     | 260 |     |     |     |     | 265 |     |     |     |     | 270 |     |     |      |
| gca | ggt | tac | agc | cgc | cag | ggt | aac | ctg | tat | gcg | ggc | gac | acc | cag | aat | 864  |
| Ala | Gly | Tyr | Ser | Arg | Gln | Gly | Asn | Leu | Tyr | Ala | Gly | Asp | Thr | Gln | Asn |      |
|     |     | 275 |     |     |     |     | 280 |     |     |     |     | 285 |     |     |     |      |
| acc | aac | tcc | gat | tcc | tat | acc | cgc | tcg | aaa | tat | ggc | gat | gaa | acc | aac | 912  |
| Thr | Asn | Ser | Asp | Ser | Tyr | Thr | Arg | Ser | Lys | Tyr | Gly | Asp | Glu | Thr | Asn |      |
|     | 290 |     |     |     |     | 295 |     |     |     |     | 300 |     |     |     |     |      |
| cgt | ctg | tat | cgc | cag | aac | tac | gcg | ctg | acc | tgg | aac | ggt | ggc | tgg | gat | 960  |
| Arg | Leu | Tyr | Arg | Gln | Asn | Tyr | Ala | Leu | Thr | Trp | Asn | Gly | Gly | Trp | Asp |      |
| 305 |     |     |     |     | 310 |     |     |     |     | 315 |     |     |     |     | 320 |      |
| aac | ggc | gtg | acc | acc | agc | aac | tgg | gtg | cag | tac | gaa | cac | acc | cgt | aac | 1008 |
| Asn | Gly | Val | Thr | Thr | Ser | Asn | Trp | Val | Gln | Tyr | Glu | His | Thr | Arg | Asn |      |
|     |     |     |     | 325 |     |     |     |     | 330 |     |     |     |     | 335 |     |      |
| tcg | cgt | att | ccg | gaa | ggt | ctg | gcg | ggc | ggt | acc | gaa | ggg | aaa | ttt | aac | 1056 |
| Ser | Arg | Ile | Pro | Glu | Gly | Leu | Ala | Gly | Gly | Thr | Glu | Gly | Lys | Phe | Asn |      |
|     |     |     | 340 |     |     |     |     | 345 |     |     |     |     | 350 |     |     |      |
| gaa | aaa | gcg | aca | cag | gat | ttc | gtc | gat | atc | gat | ctt | gat | gac | gtg | atg | 1104 |
| Glu | Lys | Ala | Thr | Gln | Asp | Phe | Val | Asp | Ile | Asp | Leu | Asp | Asp | Val | Met |      |
|     |     |     |     | 355 |     |     |     |     | 360 |     |     |     |     | 365 |     |      |
| ctg | cac | agc | gaa | gtt | aac | ctg | ccg | att | gat | ttc | ctc | gtt | aac | cag | acg | 1152 |
| Leu | His | Ser | Glu | Val | Asn | Leu | Pro | Ile | Asp | Phe | Leu | Val | Asn | Gln | Thr |      |
|     | 370 |     |     |     |     | 375 |     |     |     |     | 380 |     |     |     |     |      |
| ctg | acg | ctg | ggt | acg | gag | tgg | aat | cag | caa | cgg | atg | aag | gac | tta | agt | 1200 |
| Leu | Thr | Leu | Gly | Thr | Glu | Trp | Asn | Gln | Gln | Arg | Met | Lys | Asp | Leu | Ser |      |
| 385 |     |     |     |     | 390 |     |     |     |     | 395 |     |     |     |     | 400 |      |
| tcc | aac | acc | cag | gca | ctg | acc | gga | acg | aat | acc | ggt | ggc | gct | att | gat | 1248 |
| Ser | Asn | Thr | Gln | Ala | Leu | Thr | Gly | Thr | Asn | Thr | Gly | Gly | Ala | Ile | Asp |      |
|     |     |     |     | 405 |     |     |     |     | 410 |     |     |     |     | 415 |     |      |
| ggc | gtg | agt | acc | acc | gac | cgt | agc | ccg | tat | tca | aaa | gca | gaa | att | ttc | 1296 |
| Gly | Val | Ser | Thr | Thr | Asp | Arg | Ser | Pro | Tyr | Ser | Lys | Ala | Glu | Ile | Phe |      |
|     |     |     | 420 |     |     |     |     | 425 |     |     |     |     | 430 |     |     |      |
| tcg | ctg | ttt | gcc | gaa | aac | aac | atg | gag | ctg | act | gac | agc | acc | atc | gta | 1344 |
| Ser | Leu | Phe | Ala | Glu | Asn | Asn | Met | Glu | Leu | Thr | Asp | Ser | Thr | Ile | Val |      |
|     |     | 435 |     |     |     |     | 440 |     |     |     |     | 445 |     |     |     |      |
| acg | ccg | ggg | ctg | cgt | ttc | gat | cat | cac | agt | att | gtc | ggc | aat | aac | tgg | 1392 |
| Thr | Pro | Gly | Leu | Arg | Phe | Asp | His | His | Ser | Ile | Val | Gly | Asn | Asn | Trp |      |
|     | 450 |     |     |     |     | 455 |     |     |     |     | 460 |     |     |     |     |      |
| agc | ccg | gcg | ctg | aac | ata | tcg | caa | ggt | tta | ggc | gat | gac | ttc | acg | ctg | 1440 |
| Ser | Pro | Ala | Leu | Asn | Ile | Ser | Gln | Gly | Leu | Gly | Asp | Asp | Phe | Thr | Leu |      |
| 465 |     |     |     |     | 470 |     |     |     |     | 475 |     |     |     |     | 480 |      |
| aaa | atg | ggc | atc | gcc | cgt | gct | tat | aaa | gcg | ccg | agc | ctg | tac | cag | act | 1488 |
| Lys | Met | Gly | Ile | Ala | Arg | Ala | Tyr | Lys | Ala | Pro | Ser | Leu | Tyr | Gln | Thr |      |
|     |     |     |     | 485 |     |     |     |     | 490 |     |     |     |     | 495 |     |      |
| aac | ccg | aac | tac | att | ctc | tac | agt | aaa | ggt | cag | ggt | tgc | tat | gcc | agc | 1536 |
| Asn | Pro | Asn | Tyr | Ile | Leu | Tyr | Ser | Lys | Gly | Gln | Gly | Cys | Tyr | Ala | Ser |      |
|     |     |     | 500 |     |     |     |     | 505 |     |     |     |     | 510 |     |     |      |
| gcg | ggc | ggc | tgc | tat | ctg | caa | ggt | aac | gat | gac | ctg | aaa | gca | gaa | acc | 1584 |
| Ala | Gly | Gly | Cys | Tyr | Leu | Gln | Gly | Asn | Asp | Asp | Leu | Lys | Ala | Glu | Thr |      |
|     |     | 515 |     |     |     |     | 520 |     |     |     |     | 525 |     |     |     |      |
| agc | atc | aac | aaa | gag | att | ggt | ctg | gag | ttc | aaa | cgc | gac | ggg | tgg | ctg | 1632 |

```
Ser Ile Asn Lys Glu Ile Gly Leu Glu Phe Lys Arg Asp Gly Trp Leu
    530                 535                 540 gcg ggc gtc acc tgg ttc cgt aac gat tat cgc aat aag att gaa gcg      1680
Ala Gly Val Thr Trp Phe Arg Asn Asp Tyr Arg Asn Lys Ile Glu Ala
545                 550                 555                 560 ggc tat gtg gct gta ggg caa aac gca gtc ggc acc gat ctc tat cag      1728
Gly Tyr Val Ala Val Gly Gln Asn Ala Val Gly Thr Asp Leu Tyr Gln
                565                 570                 575 tgg gat aac gtg ccg aaa gcg gtg gtt gaa ggt ctg gaa gga tcg tta      1776
Trp Asp Asn Val Pro Lys Ala Val Val Glu Gly Leu Glu Gly Ser Leu
        580                 585                 590 aac gta ccg gtt agc gaa acg gtg atg tgg acc aat aac atc act tat      1824
Asn Val Pro Val Ser Glu Thr Val Met Trp Thr Asn Asn Ile Thr Tyr
            595                 600                 605 atg ctg aag agt gaa aac aaa acc acg ggc gac cgt ttg tcg atc atc      1872
Met Leu Lys Ser Glu Asn Lys Thr Thr Gly Asp Arg Leu Ser Ile Ile
    610                 615                 620 ccg gag tat acg ttg aac tca acg ctg agc tgg cag gca cgg gaa gat      1920
Pro Glu Tyr Thr Leu Asn Ser Thr Leu Ser Trp Gln Ala Arg Glu Asp
625                 630                 635                 640 ttg tcg atg caa acg acc ttc acc tgg tac ggc aag cag cag ccg aag      1968
Leu Ser Met Gln Thr Thr Phe Thr Trp Tyr Gly Lys Gln Gln Pro Lys
                645                 650                 655 aag tac aac tat aaa ggt cag cca gcg gtt gga ccg gaa acc aaa gaa      2016
Lys Tyr Asn Tyr Lys Gly Gln Pro Ala Val Gly Pro Glu Thr Lys Glu
        660                 665                 670 att agt cct tac agc att gtt ggc ctg agc gcg acc tgg gat gtg acg      2064
Ile Ser Pro Tyr Ser Ile Val Gly Leu Ser Ala Thr Trp Asp Val Thr
            675                 680                 685 aag aat gtc agt ctg acc ggc ggc gtg gac aat ctg ttc gac aaa cgt      2112
Lys Asn Val Ser Leu Thr Gly Gly Val Asp Asn Leu Phe Asp Lys Arg
    690                 695                 700 ttg tgg cgt gcg ggt aat gcc cag acc acg ggc gat ttg gca ggg gcc      2160
Leu Trp Arg Ala Gly Asn Ala Gln Thr Thr Gly Asp Leu Ala Gly Ala
705                 710                 715                 720 aac tat atc gcc ggt gcc ggg gcg tat acc tat aac gag ccg gga cgt      2208
Asn Tyr Ile Ala Gly Ala Gly Ala Tyr Thr Tyr Asn Glu Pro Gly Arg
                725                 730                 735 acg tgg tat atg agc gta aac acc cac ttc tga                          2241
Thr Trp Tyr Met Ser Val Asn Thr His Phe
        740                 745

<210> SEQ ID NO 4
<211> LENGTH: 746
<212> TYPE: PRT
<213> ORGANISM: Escherichia coli

<400> SEQUENCE: 4

Met Asn Lys Lys Ile His Ser Leu Ala Leu Leu Val Asn Leu Gly Ile
1               5                   10                  15

Tyr Gly Val Ala Gln Ala Gln Glu Pro Thr Asp Thr Pro Val Ser His
                20                  25                  30

Asp Asp Thr Ile Val Val Thr Ala Ala Glu Gln Asn Leu Gln Ala Pro
        35                  40                  45

Gly Val Ser Thr Ile Thr Ala Asp Glu Ile Arg Lys Asn Pro Val Ala
    50                  55                  60

Arg Asp Val Ser Lys Ile Ile Arg Thr Met Pro Gly Val Asn Leu Thr
65                  70                  75                  80

Gly Asn Ser Thr Ser Gly Gln Arg Gly Asn Asn Arg Gln Ile Asp Ile
```

-continued

```
                85                  90                  95
Arg Gly Met Gly Pro Glu Asn Thr Leu Ile Leu Ile Asp Gly Lys Pro
                    100                 105                 110

Val Ser Ser Arg Asn Ser Val Arg Gln Gly Trp Arg Gly Glu Arg Asp
                    115                 120                 125

Thr Arg Gly Asp Thr Ser Trp Val Pro Pro Glu Met Ile Glu Arg Ile
        130                 135                 140

Glu Val Leu Arg Gly Pro Ala Ala Arg Tyr Gly Asn Gly Ala Ala
145                 150                 155                 160

Gly Gly Val Val Asn Ile Ile Thr Lys Lys Gly Ser Gly Glu Trp His
                    165                 170                 175

Gly Ser Trp Asp Ala Tyr Phe Asn Ala Pro Glu His Lys Glu Glu Gly
                180                 185                 190

Ala Thr Lys Arg Thr Asn Phe Ser Leu Thr Gly Pro Leu Gly Asp Glu
                195                 200                 205

Phe Ser Phe Arg Leu Tyr Gly Asn Leu Asp Lys Thr Gln Ala Asp Ala
        210                 215                 220

Trp Asp Ile Asn Gln Gly His Gln Ser Ala Arg Ala Gly Thr Tyr Ala
225                 230                 235                 240

Thr Thr Leu Pro Ala Gly Arg Glu Gly Val Ile Asn Lys Asp Ile Asn
                    245                 250                 255

Gly Val Val Arg Trp Asp Phe Ala Pro Leu Gln Ser Leu Glu Leu Glu
                260                 265                 270

Ala Gly Tyr Ser Arg Gln Gly Asn Leu Tyr Ala Gly Asp Thr Gln Asn
                275                 280                 285

Thr Asn Ser Asp Ser Tyr Thr Arg Ser Lys Tyr Gly Asp Glu Thr Asn
        290                 295                 300

Arg Leu Tyr Arg Gln Asn Tyr Ala Leu Thr Trp Asn Gly Gly Trp Asp
305                 310                 315                 320

Asn Gly Val Thr Thr Ser Asn Trp Val Gln Tyr Glu His Thr Arg Asn
                    325                 330                 335

Ser Arg Ile Pro Glu Gly Leu Ala Gly Gly Thr Glu Gly Lys Phe Asn
                340                 345                 350

Glu Lys Ala Thr Gln Asp Phe Val Asp Ile Asp Leu Asp Asp Val Met
                355                 360                 365

Leu His Ser Glu Val Asn Leu Pro Ile Asp Phe Leu Val Asn Gln Thr
        370                 375                 380

Leu Thr Leu Gly Thr Glu Trp Asn Gln Gln Arg Met Lys Asp Leu Ser
385                 390                 395                 400

Ser Asn Thr Gln Ala Leu Thr Gly Thr Asn Thr Gly Gly Ala Ile Asp
                    405                 410                 415

Gly Val Ser Thr Thr Asp Arg Ser Pro Tyr Ser Lys Ala Glu Ile Phe
                420                 425                 430

Ser Leu Phe Ala Glu Asn Asn Met Glu Leu Thr Asp Ser Thr Ile Val
                435                 440                 445

Thr Pro Gly Leu Arg Phe Asp His His Ser Ile Val Gly Asn Asn Trp
        450                 455                 460

Ser Pro Ala Leu Asn Ile Ser Gln Gly Leu Gly Asp Asp Phe Thr Leu
465                 470                 475                 480

Lys Met Gly Ile Ala Arg Ala Tyr Lys Ala Pro Ser Leu Tyr Gln Thr
                    485                 490                 495

Asn Pro Asn Tyr Ile Leu Tyr Ser Lys Gly Gln Gly Cys Tyr Ala Ser
                500                 505                 510
```

Ala Gly Gly Cys Tyr Leu Gln Gly Asn Asp Asp Leu Lys Ala Glu Thr
         515                 520                 525

Ser Ile Asn Lys Glu Ile Gly Leu Glu Phe Lys Arg Asp Gly Trp Leu
         530                 535                 540

Ala Gly Val Thr Trp Phe Arg Asn Asp Tyr Arg Asn Lys Ile Glu Ala
545                 550                 555                 560

Gly Tyr Val Ala Val Gly Gln Asn Ala Val Gly Thr Asp Leu Tyr Gln
                565                 570                 575

Trp Asp Asn Val Pro Lys Ala Val Val Glu Gly Leu Glu Gly Ser Leu
                580                 585                 590

Asn Val Pro Val Ser Glu Thr Val Met Trp Thr Asn Asn Ile Thr Tyr
            595                 600                 605

Met Leu Lys Ser Glu Asn Lys Thr Thr Gly Asp Arg Leu Ser Ile Ile
        610                 615                 620

Pro Glu Tyr Thr Leu Asn Ser Thr Leu Ser Trp Gln Ala Arg Glu Asp
625                 630                 635                 640

Leu Ser Met Gln Thr Thr Phe Thr Trp Tyr Gly Lys Gln Gln Pro Lys
                645                 650                 655

Lys Tyr Asn Tyr Lys Gly Gln Pro Ala Val Gly Pro Glu Thr Lys Glu
                660                 665                 670

Ile Ser Pro Tyr Ser Ile Val Gly Leu Ser Ala Thr Trp Asp Val Thr
            675                 680                 685

Lys Asn Val Ser Leu Thr Gly Gly Val Asp Asn Leu Phe Asp Lys Arg
        690                 695                 700

Leu Trp Arg Ala Gly Asn Ala Gln Thr Thr Gly Asp Leu Ala Gly Ala
705                 710                 715                 720

Asn Tyr Ile Ala Gly Ala Gly Ala Tyr Thr Tyr Asn Glu Pro Gly Arg
                725                 730                 735

Thr Trp Tyr Met Ser Val Asn Thr His Phe
            740                 745

<210> SEQ ID NO 5
<211> LENGTH: 21
<212> TYPE: DNA
<213> ORGANISM: Artificial sequence
<220> FEATURE:
<223> OTHER INFORMATION: 5'-primer for tonB

<400> SEQUENCE: 5
atttgaaagg gcgaagatct g                                       21

<210> SEQ ID NO 6
<211> LENGTH: 21
<212> TYPE: DNA
<213> ORGANISM: Artificial sequence
<220> FEATURE:
<223> OTHER INFORMATION: 3'-primer for tonB

<400> SEQUENCE: 6
ttgatcctga aggaaaacct c                                       21

<210> SEQ ID NO 7
<211> LENGTH: 20
<212> TYPE: DNA
<213> ORGANISM: Artificial sequence
<220> FEATURE:
<223> OTHER INFORMATION: 5'-primer for fepA

<400> SEQUENCE: 7

```
ccaccagaaa gtgacctcaa                                                    20

<210> SEQ ID NO 8
<211> LENGTH: 21
<212> TYPE: DNA
<213> ORGANISM: Artificial sequence
<220> FEATURE:
<223> OTHER INFORMATION: 3'-primer for fepA

<400> SEQUENCE: 8
ccagagtaaa tcctgctcac a                                                  21

<210> SEQ ID NO 9
<211> LENGTH: 2325
<212> TYPE: DNA
<213> ORGANISM: Escherichia coli
<220> FEATURE:
<221> NAME/KEY: CDS
<222> LOCATION: (1)..(2322)

<400> SEQUENCE: 9 atg acg ccg tta cgc gtt ttt cgt aaa aca aca cct ttg gtt aac acc         48
Met Thr Pro Leu Arg Val Phe Arg Lys Thr Thr Pro Leu Val Asn Thr
1               5                   10                  15 att cgc ctg agc ctg ctg ccg ctg gcc ggt ctc tcg ttt tcc gct ttt         96
Ile Arg Leu Ser Leu Leu Pro Leu Ala Gly Leu Ser Phe Ser Ala Phe
            20                  25                  30 gct gca cag gtt aat atc gca ccg gga tcg ctc gat aaa gcg ctc aat        144
Ala Ala Gln Val Asn Ile Ala Pro Gly Ser Leu Asp Lys Ala Leu Asn
        35                  40                  45 cag tat gcc gca cac agc gga ttt acc ctc tcg gtt gac gcc agc ctg        192
Gln Tyr Ala Ala His Ser Gly Phe Thr Leu Ser Val Asp Ala Ser Leu
    50                  55                  60 acg cgc ggc aag cag agc aac ggc ctg cac ggc gat tac gac gtc gag        240
Thr Arg Gly Lys Gln Ser Asn Gly Leu His Gly Asp Tyr Asp Val Glu
65                  70                  75                  80 agc ggc ctg caa caa ctg ctg gac ggc agc gga ctg cag gta aaa ccg        288
Ser Gly Leu Gln Gln Leu Leu Asp Gly Ser Gly Leu Gln Val Lys Pro
                85                  90                  95 ctg gga aat aac agc tgg acg ctg gag ccc gcg ccc gca cca aaa gaa        336
Leu Gly Asn Asn Ser Trp Thr Leu Glu Pro Ala Pro Ala Pro Lys Glu
            100                 105                 110 gat gcc ctg acc gtg gtc ggc gac tgg ctg ggt gat gcg cgt gaa aac        384
Asp Ala Leu Thr Val Val Gly Asp Trp Leu Gly Asp Ala Arg Glu Asn
        115                 120                 125 gac gta ttt gaa cat gct ggc gcg cgt gac gtg atc cgc cgt gag gat        432
Asp Val Phe Glu His Ala Gly Ala Arg Asp Val Ile Arg Arg Glu Asp
    130                 135                 140 ttc gcc aaa acc ggc gca acc acc atg cgt gag gta ctt aac cgc atc        480
Phe Ala Lys Thr Gly Ala Thr Thr Met Arg Glu Val Leu Asn Arg Ile
145                 150                 155                 160 cct ggc gtc agc gcg ccg gaa aac aac ggc acc ggc agc cac gac ctg        528
Pro Gly Val Ser Ala Pro Glu Asn Asn Gly Thr Gly Ser His Asp Leu
                165                 170                 175 gcg atg aac ttt ggc atc cgg ggc ctg aac ccg cgc ctc gcc agc cgc        576
Ala Met Asn Phe Gly Ile Arg Gly Leu Asn Pro Arg Leu Ala Ser Arg
            180                 185                 190 tcg acc gtc ctg atg gac ggc atc ccc gtc ccc ttc gcc cct tac ggt        624
Ser Thr Val Leu Met Asp Gly Ile Pro Val Pro Phe Ala Pro Tyr Gly
        195                 200                 205 cag ccg cag ctt tca ctg gct ccc gtt tcg ctc ggc aac atg gat gcc        672
```

```
Gln Pro Gln Leu Ser Leu Ala Pro Val Ser Leu Gly Asn Met Asp Ala
    210             215             220 att gac gtg gta cgc ggt ggt ggt gcg gtg cgt tac gga ccg cag agc        720
Ile Asp Val Val Arg Gly Gly Gly Ala Val Arg Tyr Gly Pro Gln Ser
225             230             235             240 gtg ggc ggc gtg gtg aac ttt gtt acc cgt gcc att ccg cag gac ttt        768
Val Gly Gly Val Val Asn Phe Val Thr Arg Ala Ile Pro Gln Asp Phe
                245             250             255 ggt atc gag gcg ggc gtg gaa ggt cag ctc agc cca acc tct tca caa        816
Gly Ile Glu Ala Gly Val Glu Gly Gln Leu Ser Pro Thr Ser Ser Gln
        260             265             270 aac aac ccg aaa gag acg cac aac ctg atg gtg ggc ggc aca gcg gac        864
Asn Asn Pro Lys Glu Thr His Asn Leu Met Val Gly Gly Thr Ala Asp
            275             280             285 aac ggt ttt ggc acc gcg ctg ctc tac tcc ggc acg cgc ggc agt gac        912
Asn Gly Phe Gly Thr Ala Leu Leu Tyr Ser Gly Thr Arg Gly Ser Asp
290             295             300 tgg cgc gag cac agc gcc acc cgc atc gac gac ctg atg ctg aaa agc        960
Trp Arg Glu His Ser Ala Thr Arg Ile Asp Asp Leu Met Leu Lys Ser
305             310             315             320 aaa tat gcg ccg gat gag gtg cac acc ttc aac agc ctg ctg caa tat       1008
Lys Tyr Ala Pro Asp Glu Val His Thr Phe Asn Ser Leu Leu Gln Tyr
                325             330             335 tac gac ggt gaa gcc gac atg ccc ggt ggc ctg tct cgc gcg gat tac       1056
Tyr Asp Gly Glu Ala Asp Met Pro Gly Gly Leu Ser Arg Ala Asp Tyr
        340             345             350 gac gcc gat cgc tgg caa tcc acc cgc ccg tat gac cgc ttc tgg ggt       1104
Asp Ala Asp Arg Trp Gln Ser Thr Arg Pro Tyr Asp Arg Phe Trp Gly
            355             360             365 cgt cgc aag ctg gcg agc ctg ggc tac cag ttc cag cca gac agc cag       1152
Arg Arg Lys Leu Ala Ser Leu Gly Tyr Gln Phe Gln Pro Asp Ser Gln
370             375             380 cat aaa ttc aac att cag ggg ttc tac acc caa acc ctg cgc agc ggc       1200
His Lys Phe Asn Ile Gln Gly Phe Tyr Thr Gln Thr Leu Arg Ser Gly
385             390             395             400 tac ctg gag caa ggc aaa cgc atc acc ctc tcg ccg cgt aac tac tgg       1248
Tyr Leu Glu Gln Gly Lys Arg Ile Thr Leu Ser Pro Arg Asn Tyr Trp
                405             410             415 gtg cgc ggt att gag cca cgc tac agc cag atc ttt atg atc ggc cct       1296
Val Arg Gly Ile Glu Pro Arg Tyr Ser Gln Ile Phe Met Ile Gly Pro
        420             425             430 tcc gcg cac gaa gtg ggc gtg ggc tat cgc tat ttg aat gaa tca acg       1344
Ser Ala His Glu Val Gly Val Gly Tyr Arg Tyr Leu Asn Glu Ser Thr
            435             440             445 cat gaa atg cgt tac tac acc gcc acc agc agc ggg cag ttg ccg tcc       1392
His Glu Met Arg Tyr Tyr Thr Ala Thr Ser Ser Gly Gln Leu Pro Ser
450             455             460 ggc tca agc cct tac gac cgc gat acg cgt tcc ggc acc gag gcg cac       1440
Gly Ser Ser Pro Tyr Asp Arg Asp Thr Arg Ser Gly Thr Glu Ala His
465             470             475             480 gcc tgg tat ctg gat gac aaa atc gac atc ggc aac tgg acc atc acg       1488
Ala Trp Tyr Leu Asp Asp Lys Ile Asp Ile Gly Asn Trp Thr Ile Thr
                485             490             495 ccg ggt atg cgt ttc gaa cat atc gag tca tac cag aac aac gcc atc       1536
Pro Gly Met Arg Phe Glu His Ile Glu Ser Tyr Gln Asn Asn Ala Ile
        500             505             510 aca ggc acg cac gaa gaa gtg agc tat aac gca ccg ctt ccg gcg ttg       1584
Thr Gly Thr His Glu Glu Val Ser Tyr Asn Ala Pro Leu Pro Ala Leu
            515             520             525
```

```
aac gtg ctc tat cac ctg act gac agc tgg aat ctt tat gca aac act    1632
Asn Val Leu Tyr His Leu Thr Asp Ser Trp Asn Leu Tyr Ala Asn Thr
        530                 535                 540 gaa ggc tcg ttc ggc acc gta cag tac agc cag att ggc aag gct gtg    1680
Glu Gly Ser Phe Gly Thr Val Gln Tyr Ser Gln Ile Gly Lys Ala Val
545                 550                 555                 560 caa agc ggc aat gtt gaa ccg gaa aaa gcg cga acc tgg gaa ctc ggt    1728
Gln Ser Gly Asn Val Glu Pro Glu Lys Ala Arg Thr Trp Glu Leu Gly
                565                 570                 575 acc cgc tac gac gac ggc gcg ctg acg gcg gaa atg ggg ctg ttc ctg    1776
Thr Arg Tyr Asp Asp Gly Ala Leu Thr Ala Glu Met Gly Leu Phe Leu
            580                 585                 590 att aac ttt aac aat cag tac gac tcc aac cag acc aac gac acc gtc    1824
Ile Asn Phe Asn Asn Gln Tyr Asp Ser Asn Gln Thr Asn Asp Thr Val
        595                 600                 605 act gca cgt ggc aaa acg cgc cat acc ggg ctg gaa acg cag gca cgt    1872
Thr Ala Arg Gly Lys Thr Arg His Thr Gly Leu Glu Thr Gln Ala Arg
610                 615                 620 tac gat ctg ggt acg cta acg cca acg ctt gat aac gtt tcc atc tac    1920
Tyr Asp Leu Gly Thr Leu Thr Pro Thr Leu Asp Asn Val Ser Ile Tyr
625                 630                 635                 640 gcc agc tat gcg tat gtg aac gcg gaa atc cgc gag aaa ggc gac acc    1968
Ala Ser Tyr Ala Tyr Val Asn Ala Glu Ile Arg Glu Lys Gly Asp Thr
                645                 650                 655 tac ggc aat ctg gta cca ttc tcc ccg aaa cat aaa ggc acg ctg ggc    2016
Tyr Gly Asn Leu Val Pro Phe Ser Pro Lys His Lys Gly Thr Leu Gly
            660                 665                 670 gtg gac tac aag cca gga aac tgg acg ttc aat ctg aac agc gat ttc    2064
Val Asp Tyr Lys Pro Gly Asn Trp Thr Phe Asn Leu Asn Ser Asp Phe
        675                 680                 685 cag tcc agc cag ttt gcg gat aac gcc aat acg gtg aaa gag agc gcc    2112
Gln Ser Ser Gln Phe Ala Asp Asn Ala Asn Thr Val Lys Glu Ser Ala
690                 695                 700 gac ggc agt acc ggc cgc att ccc ggc ttc atg ctc tgg ggc gca cgc    2160
Asp Gly Ser Thr Gly Arg Ile Pro Gly Phe Met Leu Trp Gly Ala Arg
705                 710                 715                 720 gtg gcg tat gac ttt ggc ccg cag atg gca gat ctg aac ctg gca ttc    2208
Val Ala Tyr Asp Phe Gly Pro Gln Met Ala Asp Leu Asn Leu Ala Phe
                725                 730                 735 ggt gtg aaa aac atc ttc gac cag gac tac ttc atc cgc tct tat gac    2256
Gly Val Lys Asn Ile Phe Asp Gln Asp Tyr Phe Ile Arg Ser Tyr Asp
            740                 745                 750 gac aac aac aaa ggc atc tat gca ggc cag ccg cgc acg ctg tat atg    2304
Asp Asn Asn Lys Gly Ile Tyr Ala Gly Gln Pro Arg Thr Leu Tyr Met
        755                 760                 765 cag ggg tcg ttg aag ttc tga                                        2325
Gln Gly Ser Leu Lys Phe
    770

<210> SEQ ID NO 10
<211> LENGTH: 774
<212> TYPE: PRT
<213> ORGANISM: Escherichia coli

<400> SEQUENCE: 10

Met Thr Pro Leu Arg Val Phe Arg Lys Thr Thr Pro Leu Val Asn Thr
1               5                   10                  15

Ile Arg Leu Ser Leu Leu Pro Leu Ala Gly Leu Ser Phe Ser Ala Phe
            20                  25                  30

Ala Ala Gln Val Asn Ile Ala Pro Gly Ser Leu Asp Lys Ala Leu Asn
```

```
            35                  40                  45
Gln Tyr Ala Ala His Ser Gly Phe Thr Leu Ser Val Asp Ala Ser Leu
 50                  55                  60
Thr Arg Gly Lys Gln Ser Asn Gly Leu His Gly Asp Tyr Asp Val Glu
65                  70                  75                  80
Ser Gly Leu Gln Gln Leu Leu Asp Gly Ser Gly Leu Gln Val Lys Pro
                85                  90                  95
Leu Gly Asn Asn Ser Trp Thr Leu Glu Pro Ala Pro Ala Pro Lys Glu
               100                 105                 110
Asp Ala Leu Thr Val Val Gly Asp Trp Leu Gly Asp Ala Arg Glu Asn
           115                 120                 125
Asp Val Phe Glu His Ala Gly Ala Arg Asp Val Ile Arg Arg Glu Asp
           130                 135                 140
Phe Ala Lys Thr Gly Ala Thr Thr Met Arg Glu Val Leu Asn Arg Ile
145                 150                 155                 160
Pro Gly Val Ser Ala Pro Glu Asn Asn Gly Thr Gly Ser His Asp Leu
                165                 170                 175
Ala Met Asn Phe Gly Ile Arg Gly Leu Asn Pro Arg Leu Ala Ser Arg
            180                 185                 190
Ser Thr Val Leu Met Asp Gly Ile Pro Val Pro Phe Ala Pro Tyr Gly
        195                 200                 205
Gln Pro Gln Leu Ser Leu Ala Pro Val Ser Leu Gly Asn Met Asp Ala
210                 215                 220
Ile Asp Val Val Arg Gly Gly Ala Val Arg Tyr Gly Pro Gln Ser
225                 230                 235                 240
Val Gly Gly Val Val Asn Phe Val Thr Arg Ala Ile Pro Gln Asp Phe
                245                 250                 255
Gly Ile Glu Ala Gly Val Glu Gly Gln Leu Ser Pro Thr Ser Ser Gln
            260                 265                 270
Asn Asn Pro Lys Glu Thr His Asn Leu Met Val Gly Gly Thr Ala Asp
        275                 280                 285
Asn Gly Phe Gly Thr Ala Leu Leu Tyr Ser Gly Thr Arg Gly Ser Asp
290                 295                 300
Trp Arg Glu His Ser Ala Thr Arg Ile Asp Asp Leu Met Leu Lys Ser
305                 310                 315                 320
Lys Tyr Ala Pro Asp Glu Val His Thr Phe Asn Ser Leu Leu Gln Tyr
                325                 330                 335
Tyr Asp Gly Glu Ala Asp Met Pro Gly Gly Leu Ser Arg Ala Asp Tyr
            340                 345                 350
Asp Ala Asp Arg Trp Gln Ser Thr Arg Pro Tyr Asp Arg Phe Trp Gly
        355                 360                 365
Arg Arg Lys Leu Ala Ser Leu Gly Tyr Gln Phe Gln Pro Asp Ser Gln
    370                 375                 380
His Lys Phe Asn Ile Gln Gly Phe Tyr Thr Gln Thr Leu Arg Ser Gly
385                 390                 395                 400
Tyr Leu Glu Gln Gly Lys Arg Ile Thr Leu Ser Pro Arg Asn Tyr Trp
                405                 410                 415
Val Arg Gly Ile Glu Pro Arg Tyr Ser Gln Ile Phe Met Ile Gly Pro
            420                 425                 430
Ser Ala His Glu Val Gly Val Gly Tyr Arg Tyr Leu Asn Glu Ser Thr
        435                 440                 445
His Glu Met Arg Tyr Tyr Thr Ala Thr Ser Ser Gly Gln Leu Pro Ser
    450                 455                 460
```

Gly Ser Ser Pro Tyr Asp Arg Asp Thr Arg Ser Gly Thr Glu Ala His
465                 470                 475                 480

Ala Trp Tyr Leu Asp Asp Lys Ile Asp Ile Gly Asn Trp Thr Ile Thr
                485                 490                 495

Pro Gly Met Arg Phe Glu His Ile Glu Ser Tyr Gln Asn Asn Ala Ile
            500                 505                 510

Thr Gly Thr His Glu Glu Val Ser Tyr Asn Ala Pro Leu Pro Ala Leu
        515                 520                 525

Asn Val Leu Tyr His Leu Thr Asp Ser Trp Asn Leu Tyr Ala Asn Thr
    530                 535                 540

Glu Gly Ser Phe Gly Thr Val Gln Tyr Ser Gln Ile Gly Lys Ala Val
545                 550                 555                 560

Gln Ser Gly Asn Val Glu Pro Glu Lys Ala Arg Thr Trp Glu Leu Gly
                565                 570                 575

Thr Arg Tyr Asp Asp Gly Ala Leu Thr Ala Glu Met Gly Leu Phe Leu
            580                 585                 590

Ile Asn Phe Asn Asn Gln Tyr Asp Ser Asn Gln Thr Asn Asp Thr Val
        595                 600                 605

Thr Ala Arg Gly Lys Thr Arg His Thr Gly Leu Glu Thr Gln Ala Arg
    610                 615                 620

Tyr Asp Leu Gly Thr Leu Thr Pro Thr Leu Asp Asn Val Ser Ile Tyr
625                 630                 635                 640

Ala Ser Tyr Ala Tyr Val Asn Ala Glu Ile Arg Glu Lys Gly Asp Thr
                645                 650                 655

Tyr Gly Asn Leu Val Pro Phe Ser Pro Lys His Lys Gly Thr Leu Gly
            660                 665                 670

Val Asp Tyr Lys Pro Gly Asn Trp Thr Phe Asn Leu Asn Ser Asp Phe
        675                 680                 685

Gln Ser Ser Gln Phe Ala Asp Asn Ala Asn Thr Val Lys Glu Ser Ala
    690                 695                 700

Asp Gly Ser Thr Gly Arg Ile Pro Gly Phe Met Leu Trp Gly Ala Arg
705                 710                 715                 720

Val Ala Tyr Asp Phe Gly Pro Gln Met Ala Asp Leu Asn Leu Ala Phe
                725                 730                 735

Gly Val Lys Asn Ile Phe Asp Gln Asp Tyr Phe Ile Arg Ser Tyr Asp
            740                 745                 750

Asp Asn Asn Lys Gly Ile Tyr Ala Gly Gln Pro Arg Thr Leu Tyr Met
        755                 760                 765

Gln Gly Ser Leu Lys Phe
    770

<210> SEQ ID NO 11
<211> LENGTH: 2142
<212> TYPE: DNA
<213> ORGANISM: Escherichia coli
<220> FEATURE:
<221> NAME/KEY: CDS
<222> LOCATION: (1)..(2139)

<400> SEQUENCE: 11 atg aac atc att gcc att atg gga ccg cat ggc gtc ttt tat aaa gat      48
Met Asn Ile Ile Ala Ile Met Gly Pro His Gly Val Phe Tyr Lys Asp
1               5                   10                  15 gag ccc atc aaa gaa ctg gag tcg gcg ctg gtg gcg caa ggc ttt cag      96
Glu Pro Ile Lys Glu Leu Glu Ser Ala Leu Val Ala Gln Gly Phe Gln
            20                  25                  30

```
att atc tgg cca caa aac agc gtt gat ttg ctg aaa ttt atc gag cat     144
Ile Ile Trp Pro Gln Asn Ser Val Asp Leu Leu Lys Phe Ile Glu His
        35                  40                  45 aac cct cga att tgc ggc gtg att ttt gac tgg gat gag tac agt ctc     192
Asn Pro Arg Ile Cys Gly Val Ile Phe Asp Trp Asp Glu Tyr Ser Leu
    50                  55                  60 gat tta tgt agc gat atc aat cag ctt aat gaa tat ctc ccg ctt tat     240
Asp Leu Cys Ser Asp Ile Asn Gln Leu Asn Glu Tyr Leu Pro Leu Tyr
65                  70                  75                  80 gcc ttc atc aac acc cac tcg acg atg gat gtc agc gtg cag gat atg     288
Ala Phe Ile Asn Thr His Ser Thr Met Asp Val Ser Val Gln Asp Met
                85                  90                  95 cgg atg gcg ctc tgg ttt ttt gaa tat gcg ctg ggg cag gcg gaa gat     336
Arg Met Ala Leu Trp Phe Phe Glu Tyr Ala Leu Gly Gln Ala Glu Asp
            100                 105                 110 atc gcc att cgt atg cgt cag tac acc gac gaa tat ctt gat aac att     384
Ile Ala Ile Arg Met Arg Gln Tyr Thr Asp Glu Tyr Leu Asp Asn Ile
        115                 120                 125 aca ccg ccg ttc acg aaa gcc ttg ttt acc tac gtc aaa gag cgg aag     432
Thr Pro Pro Phe Thr Lys Ala Leu Phe Thr Tyr Val Lys Glu Arg Lys
    130                 135                 140 tac acc ttt tgt acg ccg ggg cat atg ggc ggc acc gca tat caa aaa     480
Tyr Thr Phe Cys Thr Pro Gly His Met Gly Gly Thr Ala Tyr Gln Lys
145                 150                 155                 160 agc ccg gtt ggc tgt ctg ttt tat gat ttt ttc ggc ggg aat act ctt     528
Ser Pro Val Gly Cys Leu Phe Tyr Asp Phe Phe Gly Gly Asn Thr Leu
                165                 170                 175 aag gct gat gtc tct att tcg gtc acc gag ctt ggt tcg ttg ctc gac     576
Lys Ala Asp Val Ser Ile Ser Val Thr Glu Leu Gly Ser Leu Leu Asp
            180                 185                 190 cac acc ggg cca cac ctg gaa gcg gaa gag tac atc gcg cgg act ttt     624
His Thr Gly Pro His Leu Glu Ala Glu Glu Tyr Ile Ala Arg Thr Phe
        195                 200                 205 ggc gcg gaa cag agt tat atc gtt acc aac gga aca tcg acg tcg aac     672
Gly Ala Glu Gln Ser Tyr Ile Val Thr Asn Gly Thr Ser Thr Ser Asn
    210                 215                 220 aaa att gtg ggt atg tac gcc gcg cca tcc ggc agt acg ctg ttg atc     720
Lys Ile Val Gly Met Tyr Ala Ala Pro Ser Gly Ser Thr Leu Leu Ile
225                 230                 235                 240 gac cgc aat tgt cat aaa tcg ctg gcg cat ctg ttg atg atg aac gat     768
Asp Arg Asn Cys His Lys Ser Leu Ala His Leu Leu Met Met Asn Asp
                245                 250                 255 gta gtg cca gtc tgg ctg aaa ccg acg cgt aat gcg ttg ggg att ctt     816
Val Val Pro Val Trp Leu Lys Pro Thr Arg Asn Ala Leu Gly Ile Leu
            260                 265                 270 ggt ggg atc ccg cgc cgt gaa ttt act cgc gac agc atc gaa gag aaa     864
Gly Gly Ile Pro Arg Arg Glu Phe Thr Arg Asp Ser Ile Glu Glu Lys
        275                 280                 285 gtc gct gct acc acg caa gca caa tgg ccg gtt cat gcg gtg atc acc     912
Val Ala Ala Thr Thr Gln Ala Gln Trp Pro Val His Ala Val Ile Thr
    290                 295                 300 aac tcc acc tat gat ggc ttg ctc tac aac acc gac tgg atc aaa cag     960
Asn Ser Thr Tyr Asp Gly Leu Leu Tyr Asn Thr Asp Trp Ile Lys Gln
305                 310                 315                 320 acg ctg gat gtc ccg tcg att cac ttc gat tct gcc tgg gtg ccg tac    1008
Thr Leu Asp Val Pro Ser Ile His Phe Asp Ser Ala Trp Val Pro Tyr
                325                 330                 335 acc cat ttt cat ccg atc tac cag ggt aaa agt ggt atg agc ggc gag    1056
Thr His Phe His Pro Ile Tyr Gln Gly Lys Ser Gly Met Ser Gly Glu
```

-continued

|  |  |  |  |  |  |  |  |  |  |  |  |  |  |  |  |
|---|---|---|---|---|---|---|---|---|---|---|---|---|---|---|---|
|  |  | 340 |  |  |  | 345 |  |  |  | 350 |  |  |  |  |  |
| cgt | gtt | gcg | gga | aaa | gtg | atc | ttc | gaa | acg | caa | tcg | acc | cac | aaa | atg | 1104 |
| Arg | Val | Ala | Gly | Lys | Val | Ile | Phe | Glu | Thr | Gln | Ser | Thr | His | Lys | Met |  |
|  |  | 355 |  |  |  | 360 |  |  |  | 365 |  |  |  |  |  |
| ctg | gcg | gcg | tta | tcg | cag | gct | tcg | ctg | atc | cac | att | aaa | ggc | gag | tat | 1152 |
| Leu | Ala | Ala | Leu | Ser | Gln | Ala | Ser | Leu | Ile | His | Ile | Lys | Gly | Glu | Tyr |  |
| 370 |  |  |  | 375 |  |  |  |  | 380 |  |  |  |  |  |  |
| gac | gaa | gag | gcc | ttt | aac | gaa | gcc | ttt | atg | atg | cat | acc | acc | acc | tcg | 1200 |
| Asp | Glu | Glu | Ala | Phe | Asn | Glu | Ala | Phe | Met | Met | His | Thr | Thr | Thr | Ser |  |
| 385 |  |  |  |  | 390 |  |  |  |  | 395 |  |  |  |  | 400 |
| ccc | agt | tat | ccc | att | gtt | gct | tcg | gtt | gag | acg | gcg | gcg | gcg | atg | ctg | 1248 |
| Pro | Ser | Tyr | Pro | Ile | Val | Ala | Ser | Val | Glu | Thr | Ala | Ala | Ala | Met | Leu |  |
|  |  |  |  | 405 |  |  |  |  | 410 |  |  |  |  | 415 |  |
| cgt | ggt | aat | ccg | ggc | aaa | cgg | ctg | att | aac | cgt | tca | gta | gaa | cga | gct | 1296 |
| Arg | Gly | Asn | Pro | Gly | Lys | Arg | Leu | Ile | Asn | Arg | Ser | Val | Glu | Arg | Ala |  |
|  |  |  | 420 |  |  |  |  | 425 |  |  |  |  | 430 |  |  |
| ctg | cat | ttt | cgc | aaa | gag | gtc | cag | cgg | ctg | cgg | gaa | gag | tct | gac | ggt | 1344 |
| Leu | His | Phe | Arg | Lys | Glu | Val | Gln | Arg | Leu | Arg | Glu | Glu | Ser | Asp | Gly |  |
|  |  |  | 435 |  |  |  |  | 440 |  |  |  |  | 445 |  |  |
| tgg | ttt | ttc | gat | atc | tgg | caa | ccg | ccg | cag | gtg | gat | gaa | gcc | gaa | tgc | 1392 |
| Trp | Phe | Phe | Asp | Ile | Trp | Gln | Pro | Pro | Gln | Val | Asp | Glu | Ala | Glu | Cys |  |
| 450 |  |  |  |  | 455 |  |  |  |  | 460 |  |  |  |  |  |
| tgg | ccc | gtt | gcg | cct | ggc | gaa | cag | tgg | cac | ggc | ttt | aac | gat | gcg | gat | 1440 |
| Trp | Pro | Val | Ala | Pro | Gly | Glu | Gln | Trp | His | Gly | Phe | Asn | Asp | Ala | Asp |  |
| 465 |  |  |  |  | 470 |  |  |  |  | 475 |  |  |  |  | 480 |
| gcc | gat | cat | atg | ttt | ctc | gat | ccg | gtt | aaa | gtc | act | att | ttg | aca | ccg | 1488 |
| Ala | Asp | His | Met | Phe | Leu | Asp | Pro | Val | Lys | Val | Thr | Ile | Leu | Thr | Pro |  |
|  |  |  |  | 485 |  |  |  |  | 490 |  |  |  |  | 495 |  |
| ggg | atg | gac | gag | cag | ggc | aat | atg | agc | gag | gag | ggg | atc | ccg | gcg | gcg | 1536 |
| Gly | Met | Asp | Glu | Gln | Gly | Asn | Met | Ser | Glu | Glu | Gly | Ile | Pro | Ala | Ala |  |
|  |  |  | 500 |  |  |  |  | 505 |  |  |  |  | 510 |  |  |
| ctg | gta | gca | aaa | ttc | ctc | gac | gaa | cgt | ggg | atc | gta | gta | gag | aaa | acc | 1584 |
| Leu | Val | Ala | Lys | Phe | Leu | Asp | Glu | Arg | Gly | Ile | Val | Val | Glu | Lys | Thr |  |
|  |  |  | 515 |  |  |  |  | 520 |  |  |  |  | 525 |  |  |
| ggc | cct | tat | aac | ctg | ctg | ttt | ctc | ttt | agt | att | ggc | atc | gat | aaa | acc | 1632 |
| Gly | Pro | Tyr | Asn | Leu | Leu | Phe | Leu | Phe | Ser | Ile | Gly | Ile | Asp | Lys | Thr |  |
|  | 530 |  |  |  |  | 535 |  |  |  |  | 540 |  |  |  |  |
| aaa | gca | atg | gga | tta | ttg | cgt | ggg | ttg | acg | gaa | ttc | aaa | cgc | tct | tac | 1680 |
| Lys | Ala | Met | Gly | Leu | Leu | Arg | Gly | Leu | Thr | Glu | Phe | Lys | Arg | Ser | Tyr |  |
| 545 |  |  |  |  | 550 |  |  |  |  | 555 |  |  |  |  | 560 |
| gat | ctc | aac | ctg | cgg | atc | aaa | aat | atg | cta | ccc | gat | ctc | tat | gca | gaa | 1728 |
| Asp | Leu | Asn | Leu | Arg | Ile | Lys | Asn | Met | Leu | Pro | Asp | Leu | Tyr | Ala | Glu |  |
|  |  |  |  | 565 |  |  |  |  | 570 |  |  |  |  | 575 |  |
| gat | ccc | gat | ttc | tac | cgc | aat | atg | cgt | att | cag | gat | ctg | gca | caa | ggg | 1776 |
| Asp | Pro | Asp | Phe | Tyr | Arg | Asn | Met | Arg | Ile | Gln | Asp | Leu | Ala | Gln | Gly |  |
|  |  |  | 580 |  |  |  |  | 585 |  |  |  |  | 590 |  |  |
| atc | cat | aag | ctg | att | cgt | aaa | cac | gat | ctt | ccc | ggt | ttg | atg | ttg | cgg | 1824 |
| Ile | His | Lys | Leu | Ile | Arg | Lys | His | Asp | Leu | Pro | Gly | Leu | Met | Leu | Arg |  |
|  |  | 595 |  |  |  |  | 600 |  |  |  |  | 605 |  |  |  |
| gca | ttc | gat | act | ttg | ccg | gag | atg | atc | atg | acg | cca | cat | cag | gca | tgg | 1872 |
| Ala | Phe | Asp | Thr | Leu | Pro | Glu | Met | Ile | Met | Thr | Pro | His | Gln | Ala | Trp |  |
| 610 |  |  |  |  | 615 |  |  |  |  | 620 |  |  |  |  |  |
| caa | cga | caa | att | aaa | ggc | gaa | gta | gaa | acc | att | gcg | ctg | gaa | caa | ctg | 1920 |
| Gln | Arg | Gln | Ile | Lys | Gly | Glu | Val | Glu | Thr | Ile | Ala | Leu | Glu | Gln | Leu |  |
| 625 |  |  |  |  | 630 |  |  |  |  | 635 |  |  |  |  | 640 |
| gtc | ggt | aga | gta | tcg | gca | aat | atg | atc | ctg | cct | tat | cca | ccg | ggc | gta | 1968 |
| Val | Gly | Arg | Val | Ser | Ala | Asn | Met | Ile | Leu | Pro | Tyr | Pro | Pro | Gly | Val |  |
|  |  |  |  | 645 |  |  |  |  | 650 |  |  |  |  | 655 |  |
| ccg | ctg | ttg | atg | cct | gga | gaa | atg | ctg | acc | aaa | gag | agc | cgc | aca | gta | 2016 |

```
Pro Leu Leu Met Pro Gly Glu Met Leu Thr Lys Glu Ser Arg Thr Val
            660                 665                 670 ctc gat ttt cta ctg atg ctt tgt tcc gtc ggg caa cat tac ccc ggt    2064
Leu Asp Phe Leu Leu Met Leu Cys Ser Val Gly Gln His Tyr Pro Gly
        675                 680                 685 ttt gaa acg gat att cac ggc gcg aaa cag gac gaa gac ggc gtt tac    2112
Phe Glu Thr Asp Ile His Gly Ala Lys Gln Asp Glu Asp Gly Val Tyr
690                 695                 700 cgc gta cga gtc cta aaa atg gcg gga taa                            2142
Arg Val Arg Val Leu Lys Met Ala Gly
705                 710

<210> SEQ ID NO 12
<211> LENGTH: 713
<212> TYPE: PRT
<213> ORGANISM: Escherichia coli

<400> SEQUENCE: 12
```

Met Asn Ile Ile Ala Ile Met Gly Pro His Gly Val Phe Tyr Lys Asp
1               5                   10                  15

Glu Pro Ile Lys Glu Leu Glu Ser Ala Leu Val Ala Gln Gly Phe Gln
                20                  25                  30

Ile Ile Trp Pro Gln Asn Ser Val Asp Leu Leu Lys Phe Ile Glu His
            35                  40                  45

Asn Pro Arg Ile Cys Gly Val Ile Phe Asp Trp Asp Glu Tyr Ser Leu
50                  55                  60

Asp Leu Cys Ser Asp Ile Asn Gln Leu Asn Glu Tyr Leu Pro Leu Tyr
65                  70                  75                  80

Ala Phe Ile Asn Thr His Ser Thr Met Asp Val Ser Val Gln Asp Met
                85                  90                  95

Arg Met Ala Leu Trp Phe Phe Glu Tyr Ala Leu Gly Gln Ala Glu Asp
            100                 105                 110

Ile Ala Ile Arg Met Arg Gln Tyr Thr Asp Glu Tyr Leu Asp Asn Ile
        115                 120                 125

Thr Pro Pro Phe Thr Lys Ala Leu Phe Thr Tyr Val Lys Glu Arg Lys
130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Gly Asn Thr Leu
                165                 170                 175

Lys Ala Asp Val Ser Ile Ser Val Thr Glu Leu Gly Ser Leu Leu Asp
            180                 185                 190

His Thr Gly Pro His Leu Glu Ala Glu Glu Tyr Ile Ala Arg Thr Phe
        195                 200                 205

Gly Ala Glu Gln Ser Tyr Ile Val Thr Asn Gly Thr Ser Thr Ser Asn
210                 215                 220

Lys Ile Val Gly Met Tyr Ala Ala Pro Ser Gly Ser Thr Leu Leu Ile
225                 230                 235                 240

Asp Arg Asn Cys His Lys Ser Leu Ala His Leu Leu Met Met Asn Asp
                245                 250                 255

Val Val Pro Val Trp Leu Lys Pro Thr Arg Asn Ala Leu Gly Ile Leu
            260                 265                 270

Gly Gly Ile Pro Arg Arg Glu Phe Thr Arg Asp Ser Ile Glu Glu Lys
        275                 280                 285

Val Ala Ala Thr Thr Gln Ala Gln Trp Pro Val His Ala Val Ile Thr
290                 295                 300

-continued

```
Asn Ser Thr Tyr Asp Gly Leu Leu Tyr Asn Thr Asp Trp Ile Lys Gln
305                 310                 315                 320

Thr Leu Asp Val Pro Ser Ile His Phe Asp Ser Ala Trp Val Pro Tyr
                325                 330                 335

Thr His Phe His Pro Ile Tyr Gln Gly Lys Ser Gly Met Ser Gly Glu
            340                 345                 350

Arg Val Ala Gly Lys Val Ile Phe Glu Thr Gln Ser Thr His Lys Met
        355                 360                 365

Leu Ala Ala Leu Ser Gln Ala Ser Leu Ile His Ile Lys Gly Glu Tyr
    370                 375                 380

Asp Glu Glu Ala Phe Asn Glu Ala Phe Met Met His Thr Thr Thr Ser
385                 390                 395                 400

Pro Ser Tyr Pro Ile Val Ala Ser Val Glu Thr Ala Ala Ala Met Leu
                405                 410                 415

Arg Gly Asn Pro Gly Lys Arg Leu Ile Asn Arg Ser Val Glu Arg Ala
            420                 425                 430

Leu His Phe Arg Lys Glu Val Gln Arg Leu Arg Glu Glu Ser Asp Gly
        435                 440                 445

Trp Phe Phe Asp Ile Trp Gln Pro Pro Gln Val Asp Glu Ala Glu Cys
    450                 455                 460

Trp Pro Val Ala Pro Gly Glu Gln Trp His Gly Phe Asn Asp Ala Asp
465                 470                 475                 480

Ala Asp His Met Phe Leu Asp Pro Val Lys Val Thr Ile Leu Thr Pro
                485                 490                 495

Gly Met Asp Glu Gln Gly Asn Met Ser Glu Gly Ile Pro Ala Ala
            500                 505                 510

Leu Val Ala Lys Phe Leu Asp Glu Arg Gly Ile Val Val Glu Lys Thr
        515                 520                 525

Gly Pro Tyr Asn Leu Leu Phe Leu Phe Ser Ile Gly Ile Asp Lys Thr
    530                 535                 540

Lys Ala Met Gly Leu Leu Arg Gly Leu Thr Glu Phe Lys Arg Ser Tyr
545                 550                 555                 560

Asp Leu Asn Leu Arg Ile Lys Asn Met Leu Pro Asp Leu Tyr Ala Glu
                565                 570                 575

Asp Pro Asp Phe Tyr Arg Asn Met Arg Ile Gln Asp Leu Ala Gln Gly
            580                 585                 590

Ile His Lys Leu Ile Arg Lys His Asp Leu Pro Gly Leu Met Leu Arg
        595                 600                 605

Ala Phe Asp Thr Leu Pro Glu Met Ile Met Thr Pro His Gln Ala Trp
    610                 615                 620

Gln Arg Gln Ile Lys Gly Glu Val Glu Thr Ile Ala Leu Glu Gln Leu
625                 630                 635                 640

Val Gly Arg Val Ser Ala Asn Met Ile Leu Pro Tyr Pro Pro Gly Val
                645                 650                 655

Pro Leu Leu Met Pro Gly Glu Met Leu Thr Lys Glu Ser Arg Thr Val
            660                 665                 670

Leu Asp Phe Leu Leu Met Leu Cys Ser Val Gly Gln His Tyr Pro Gly
        675                 680                 685

Phe Glu Thr Asp Ile His Gly Ala Lys Gln Asp Glu Asp Gly Val Tyr
    690                 695                 700

Arg Val Arg Val Leu Lys Met Ala Gly
705                 710
```

<210> SEQ ID NO 13
<211> LENGTH: 54
<212> TYPE: DNA
<213> ORGANISM: Artificial Sequence
<220> FEATURE:
<223> OTHER INFORMATION: 5'-primer for cadA

<400> SEQUENCE: 13
tttgctttct tctttcaata ccttaacggt atagcgtgaa gcctgctttt ttat    54

<210> SEQ ID NO 14
<211> LENGTH: 54
<212> TYPE: DNA
<213> ORGANISM: Artificial Sequence
<220> FEATURE:
<223> OTHER INFORMATION: 3'-primer for cadA

<400> SEQUENCE: 14
agatatgact atgaacgtta ttgcaatatt gaatcacgct caagttagta taaa    54

<210> SEQ ID NO 15
<211> LENGTH: 54
<212> TYPE: DNA
<213> ORGANISM: Artificial Sequence
<220> FEATURE:
<223> OTHER INFORMATION: 5'-primer for ldc

<400> SEQUENCE: 15
ggaggaacac atgaacatca ttgccattat gggacctgaa gcctgctttt ttat    54

<210> SEQ ID NO 16
<211> LENGTH: 53
<212> TYPE: DNA
<213> ORGANISM: Artificial Sequence
<220> FEATURE:
<223> OTHER INFORMATION: 3'-primer for ldc

<400> SEQUENCE: 16
cgccattttt aggactcgta cgcggtaaac gccgtccgtc aagttagtat aaa    53

<210> SEQ ID NO 17
<211> LENGTH: 2148
<212> TYPE: DNA
<213> ORGANISM: Escherichia coli
<220> FEATURE:
<221> NAME/KEY: CDS
<222> LOCATION: (1)..(2145)

<400> SEQUENCE: 17

| | | | | | | | | | | | | | | | | |
|---|---|---|---|---|---|---|---|---|---|---|---|---|---|---|---|---|---|
| atg | aac | gtt | att | gca | ata | ttg | aat | cac | atg | ggg | gtt | tat | ttt | aaa | gaa | | 48 |
| Met | Asn | Val | Ile | Ala | Ile | Leu | Asn | His | Met | Gly | Val | Tyr | Phe | Lys | Glu | | |
| 1 | | | | 5 | | | | | 10 | | | | | 15 | | | |
| gaa | ccc | atc | cgt | gaa | ctt | cat | cgc | gcg | ctt | gaa | cgt | ctg | aac | ttc | cag | | 96 |
| Glu | Pro | Ile | Arg | Glu | Leu | His | Arg | Ala | Leu | Glu | Arg | Leu | Asn | Phe | Gln | | |
| | | | 20 | | | | | 25 | | | | | 30 | | | | |
| att | gtt | tac | ccg | aac | gac | cgt | gac | gac | tta | tta | aaa | ctg | atc | gaa | aac | | 144 |
| Ile | Val | Tyr | Pro | Asn | Asp | Arg | Asp | Asp | Leu | Leu | Lys | Leu | Ile | Glu | Asn | | |
| | | 35 | | | | | 40 | | | | | 45 | | | | | |
| aat | gcg | cgt | ctg | tgc | ggc | gtt | att | ttt | gac | tgg | gat | aaa | tat | aat | ctc | | 192 |
| Asn | Ala | Arg | Leu | Cys | Gly | Val | Ile | Phe | Asp | Trp | Asp | Lys | Tyr | Asn | Leu | | |
| | 50 | | | | | 55 | | | | | 60 | | | | | | |
| gag | ctg | tgc | gaa | gaa | att | agc | aaa | atg | aac | gag | aac | ctg | ccg | ttg | tac | | 240 |
| Glu | Leu | Cys | Glu | Glu | Ile | Ser | Lys | Met | Asn | Glu | Asn | Leu | Pro | Leu | Tyr | | |
| 65 | | | | | 70 | | | | | 75 | | | | | 80 | | |

```
gcg ttc gct aat acg tat tcc act ctc gat gta agc ctg aat gac ctg      288
Ala Phe Ala Asn Thr Tyr Ser Thr Leu Asp Val Ser Leu Asn Asp Leu
                85                  90                  95 cgt tta cag att agc ttc ttt gaa tat gcg ctg ggt gct gct gaa gat      336
Arg Leu Gln Ile Ser Phe Phe Glu Tyr Ala Leu Gly Ala Ala Glu Asp
            100                 105                 110 att gct aat aag atc aag cag acc act gac gaa tat atc aac act att      384
Ile Ala Asn Lys Ile Lys Gln Thr Thr Asp Glu Tyr Ile Asn Thr Ile
        115                 120                 125 ctg cct ccg ctg act aaa gca ctg ttt aaa tat gtt cgt gaa ggt aaa      432
Leu Pro Pro Leu Thr Lys Ala Leu Phe Lys Tyr Val Arg Glu Gly Lys
    130                 135                 140 tat act ttc tgt act cct ggt cac atg ggc ggt act gca ttc cag aaa      480
Tyr Thr Phe Cys Thr Pro Gly His Met Gly Gly Thr Ala Phe Gln Lys
145                 150                 155                 160 agc ccg gta ggt agc ctg ttc tat gat ttc ttt ggt ccg aat acc atg      528
Ser Pro Val Gly Ser Leu Phe Tyr Asp Phe Phe Gly Pro Asn Thr Met
                165                 170                 175 aaa tct gat att tcc att tca gta tct gaa ctg ggt tct ctg ctg gat      576
Lys Ser Asp Ile Ser Ile Ser Val Ser Glu Leu Gly Ser Leu Leu Asp
            180                 185                 190 cac agt ggt cca cac aaa gaa gca gaa cag tat atc gct cgc gtc ttt      624
His Ser Gly Pro His Lys Glu Ala Glu Gln Tyr Ile Ala Arg Val Phe
        195                 200                 205 aac gca gac cgc agc tac atg gtg acc aac ggt act tcc act gcg aac      672
Asn Ala Asp Arg Ser Tyr Met Val Thr Asn Gly Thr Ser Thr Ala Asn
    210                 215                 220 aaa att gtt ggt atg tac tct gct cca gca ggc agc acc att ctg att      720
Lys Ile Val Gly Met Tyr Ser Ala Pro Ala Gly Ser Thr Ile Leu Ile
225                 230                 235                 240 gac cgt aac tgc cac aaa tcg ctg acc cac ctg atg atg atg agc gat      768
Asp Arg Asn Cys His Lys Ser Leu Thr His Leu Met Met Met Ser Asp
                245                 250                 255 gtt acg cca atc tat ttc cgc ccg acc cgt aac gct tac ggt att ctt      816
Val Thr Pro Ile Tyr Phe Arg Pro Thr Arg Asn Ala Tyr Gly Ile Leu
            260                 265                 270 ggt ggt atc cca cag agt gaa ttc cag cac gct acc att gct aag cgc      864
Gly Gly Ile Pro Gln Ser Glu Phe Gln His Ala Thr Ile Ala Lys Arg
        275                 280                 285 gtg aaa gaa aca cca aac gca acc tgg ccg gta cat gct gta att acc      912
Val Lys Glu Thr Pro Asn Ala Thr Trp Pro Val His Ala Val Ile Thr
    290                 295                 300 aac tct acc tat gat ggt ctg cta tac aac acc gac ttc atc aag aaa      960
Asn Ser Thr Tyr Asp Gly Leu Leu Tyr Asn Thr Asp Phe Ile Lys Lys
305                 310                 315                 320 aca ctg gat gtg aaa tcc atc cac ttt gac tcc gcg tgg gtg cct tac     1008
Thr Leu Asp Val Lys Ser Ile His Phe Asp Ser Ala Trp Val Pro Tyr
                325                 330                 335 acc aac ttc tca ccg att tac gaa ggt aaa tgc ggt atg agc ggt ggc     1056
Thr Asn Phe Ser Pro Ile Tyr Glu Gly Lys Cys Gly Met Ser Gly Gly
            340                 345                 350 cgt gta gaa ggg aaa gtg att tac gaa acc cag tcc act cac aaa ctg     1104
Arg Val Glu Gly Lys Val Ile Tyr Glu Thr Gln Ser Thr His Lys Leu
        355                 360                 365 ctg gcg gcg ttc tct cag gct tcc atg atc cac gtt aaa ggt gac gta     1152
Leu Ala Ala Phe Ser Gln Ala Ser Met Ile His Val Lys Gly Asp Val
    370                 375                 380 aac gaa gaa acc ttt aac gaa gcc tac atg atg cac acc acc act tct     1200
Asn Glu Glu Thr Phe Asn Glu Ala Tyr Met Met His Thr Thr Thr Ser
385                 390                 395                 400
```

```
ccg cac tac ggt atc gtg gcg tcc act gaa acc gct gcg gcg atg atg    1248
Pro His Tyr Gly Ile Val Ala Ser Thr Glu Thr Ala Ala Ala Met Met
            405             410             415 aaa ggc aat gca ggt aag cgt ctg atc aac ggt tct att gaa cgt gcg    1296
Lys Gly Asn Ala Gly Lys Arg Leu Ile Asn Gly Ser Ile Glu Arg Ala
        420             425             430 atc aaa ttc cgt aaa gag atc aaa cgt ctg aga acg gaa tct gat ggc    1344
Ile Lys Phe Arg Lys Glu Ile Lys Arg Leu Arg Thr Glu Ser Asp Gly
        435             440             445 tgg ttc ttt gat gta tgg cag ccg gat cat atc gat acg act gaa tgc    1392
Trp Phe Phe Asp Val Trp Gln Pro Asp His Ile Asp Thr Thr Glu Cys
    450             455             460 tgg ccg ctg cgt tct gac agc acc tgg cac ggc ttc aaa aac atc gat    1440
Trp Pro Leu Arg Ser Asp Ser Thr Trp His Gly Phe Lys Asn Ile Asp
465             470             475             480 aac gag cac atg tat ctt gac ccg atc aaa gtc acc ctg ctg act ccg    1488
Asn Glu His Met Tyr Leu Asp Pro Ile Lys Val Thr Leu Leu Thr Pro
            485             490             495 ggg atg gaa aaa gac ggc acc atg agc gac ttt ggt att ccg gcc agc    1536
Gly Met Glu Lys Asp Gly Thr Met Ser Asp Phe Gly Ile Pro Ala Ser
        500             505             510 atc gtg gcg aaa tac ctc gac gaa cat ggc atc gtt gtt gag aaa acc    1584
Ile Val Ala Lys Tyr Leu Asp Glu His Gly Ile Val Val Glu Lys Thr
        515             520             525 ggt ccg tat aac ctg ctg ttc ctg ttc agc atc ggt atc gat aag acc    1632
Gly Pro Tyr Asn Leu Leu Phe Leu Phe Ser Ile Gly Ile Asp Lys Thr
    530             535             540 aaa gca ctg agc ctg ctg cgt gct ctg act gac ttt aaa cgt gcg ttc    1680
Lys Ala Leu Ser Leu Leu Arg Ala Leu Thr Asp Phe Lys Arg Ala Phe
545             550             555             560 gac ctg aac ctg cgt gtg aaa aac atg ctg ccg tct ctg tat cgt gaa    1728
Asp Leu Asn Leu Arg Val Lys Asn Met Leu Pro Ser Leu Tyr Arg Glu
            565             570             575 gat cct gaa ttc tat gaa aac atg cgt att cag gaa ctg gct cag aat    1776
Asp Pro Glu Phe Tyr Glu Asn Met Arg Ile Gln Glu Leu Ala Gln Asn
        580             585             590 atc cac aaa ctg att gtt cac cac aat ctg ccg gat ctg atg tat cgc    1824
Ile His Lys Leu Ile Val His His Asn Leu Pro Asp Leu Met Tyr Arg
        595             600             605 gca ttt gaa gtg ctg ccg acg atg gta atg act ccg tat gct gca ttc    1872
Ala Phe Glu Val Leu Pro Thr Met Val Met Thr Pro Tyr Ala Ala Phe
    610             615             620 cag aaa gag ctg cac ggt atg acc gaa gaa gtt tac ctc gac gaa atg    1920
Gln Lys Glu Leu His Gly Met Thr Glu Glu Val Tyr Leu Asp Glu Met
625             630             635             640 gta ggt cgt att aac gcc aat atg atc ctt ccg tac ccg ccg gga gtt    1968
Val Gly Arg Ile Asn Ala Asn Met Ile Leu Pro Tyr Pro Pro Gly Val
            645             650             655 cct ctg gta atg ccg ggt gaa atg atc acc gaa gaa agc cgt ccg gtt    2016
Pro Leu Val Met Pro Gly Glu Met Ile Thr Glu Glu Ser Arg Pro Val
        660             665             670 ctg gag ttc ctg cag atg ctg tgt gaa atc ggc gct cac tat ccg ggc    2064
Leu Glu Phe Leu Gln Met Leu Cys Glu Ile Gly Ala His Tyr Pro Gly
        675             680             685 ttt gaa acc gat att cac ggt gca tac cgt cag gct gat ggc cgc tat    2112
Phe Glu Thr Asp Ile His Gly Ala Tyr Arg Gln Ala Asp Gly Arg Tyr
    690             695             700 acc gtt aag gta ttg aaa gaa gaa agc aaa aaa taa                    2148
Thr Val Lys Val Leu Lys Glu Glu Ser Lys Lys
```

```
                    705                 710                 715

<210> SEQ ID NO 18
<211> LENGTH: 715
<212> TYPE: PRT
<213> ORGANISM: Escherichia coli

<400> SEQUENCE: 18

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
    290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350
```

```
Arg Val Glu Gly Lys Val Ile Tyr Glu Thr Gln Ser Thr His Lys Leu
        355                 360                 365

Leu Ala Ala Phe Ser Gln Ala Ser Met Ile His Val Lys Gly Asp Val
        370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                    405                 410                 415

Lys Gly Asn Ala Gly Lys Arg Leu Ile Asn Gly Ser Ile Glu Arg Ala
                420                 425                 430

Ile Lys Phe Arg Lys Glu Ile Lys Arg Leu Arg Thr Glu Ser Asp Gly
        435                 440                 445

Trp Phe Phe Asp Val Trp Gln Pro Asp His Ile Asp Thr Thr Glu Cys
        450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                    485                 490                 495

Gly Met Glu Lys Asp Gly Thr Met Ser Asp Phe Gly Ile Pro Ala Ser
                500                 505                 510

Ile Val Ala Lys Tyr Leu Asp Glu His Gly Ile Val Val Glu Lys Thr
        515                 520                 525

Gly Pro Tyr Asn Leu Leu Phe Leu Phe Ser Ile Gly Ile Asp Lys Thr
        530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                    565                 570                 575

Asp Pro Glu Phe Tyr Glu Asn Met Arg Ile Gln Glu Leu Ala Gln Asn
                580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
        610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                    645                 650                 655

Pro Leu Val Met Pro Gly Glu Met Ile Thr Glu Glu Ser Arg Pro Val
                660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
        690                 695                 700

Thr Val Lys Val Leu Lys Glu Glu Ser Lys Lys
705                 710                 715
```